United States Patent [19]
Piepersberg et al.

[11] Patent Number: 5,614,619
[45] Date of Patent: Mar. 25, 1997

[54] SECONDARY-METABOLITE BIOSYNTHESIS GENES FROM ACTINOMYCETES, METHOD OF ISOLATING THEM AND THEIR USE

[75] Inventors: Wolfgang Piepersberg, Wuppertal; Michael Stockmann, Bonn; Kambiz M. Taleghani, München; Jürgen Distler, Wuppertal; Susanne Grabley, Königstein; Petra Sichel, Rüsselsheim; Barbara Bräu, Frankfurt am Main, all of Germany

[73] Assignee: Hoechst Aktiengesellschaft, Frankfurt am Main, Germany

[21] Appl. No.: 196,218

[22] PCT Filed: Sep. 15, 1992

[86] PCT No.: PCT/EP92/02111

§ 371 Date: Aug. 25, 1994

§ 102(e) Date: Aug. 25, 1994

[87] PCT Pub. No.: WO93/06219

PCT Pub. Date: Apr. 1, 1993

[30] Foreign Application Priority Data

Sep. 18, 1991 [DE] Germany .................. 41 30 967.7

[51] Int. Cl.⁶ .................................................. C07H 21/04
[52] U.S. Cl. ........................................ 536/23.2; 435/320.1
[58] Field of Search .................. 435/94, 100, 172.3, 435/234, 886; 536/23.2

[56] References Cited

FOREIGN PATENT DOCUMENTS

WO87/03907  7/1987  WIPO .

OTHER PUBLICATIONS

Michael Stockmann et al., "Gene probes for the detection of 6-deoxyhexose metabolism in secondary metabolite-producing streptomycetes," FEMS Microbiology Letters 90 (1992) pp. 185–190.

Jürgen Distler et al., "Gene cluster for streptomycin biosynthesis in streptomyces griseus: nucleotide sequence of three genes and analysis of transcriptional activity," Nucleic Acids Research, vol. 15, No. 19 (1987) pp. 8041–8057.

Dekker et al. (1991) J. Bacteriol. 173: 3078–3083.

Malpartida et al. (1987) Nature 325: 818–821.

*Primary Examiner*—Robert A. Wax
*Assistant Examiner*—Lisa J. Hobbs
*Attorney, Agent, or Firm*—Finnegan, Henderson, Farabow, Garrett & Dunner, L.L.P.

[57] ABSTRACT

Secondary-metabolite biosynthesis genes from actinomycetes, method of isolating them, and their use.

The invention concerns secondary-metabolite biosynthesis genes from actinomycetes, a method of isolating secondary-metabolite and, in particular, 6-deoxy-sugar biosynthesis genes, from actinomycetes using the gene probes strD, strE, strL and strM gene probes from *Streptomyces griseus* DSM40236, and structurally related genes, as gene probes for detecting the genes snoT (coding for amphotheronolide B-dTDP-D-mycosaminyl transferase), snoD (coding for dTDP-D-glucose synthase) and snoM (coding for dTDP-4-keto-6-deoxy-D-glucose isomerase), or one or more secondary-metabolite biosynthesis genes from actinomycetes. The invention also concerns the use of secondary-metabolite biosynthesis genes thus isolated.

2 Claims, 12 Drawing Sheets

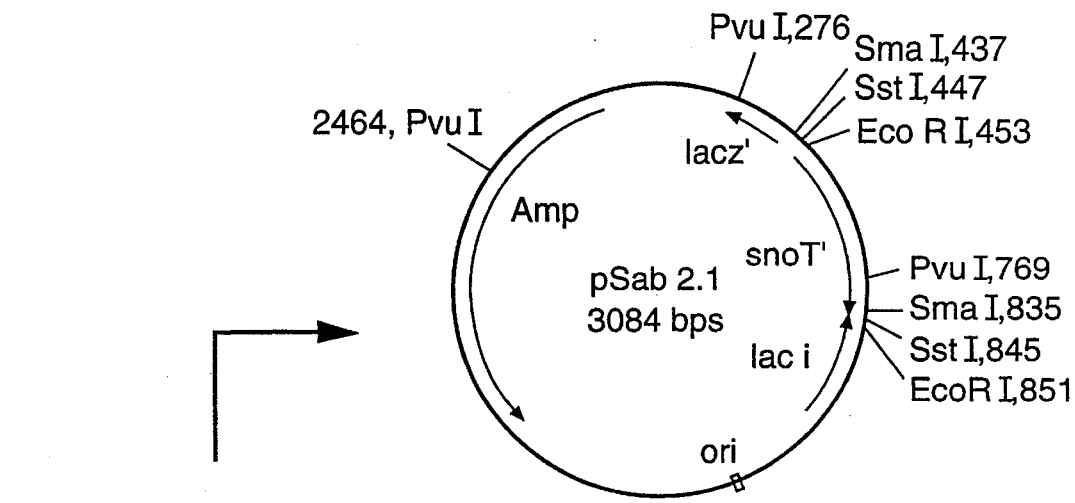
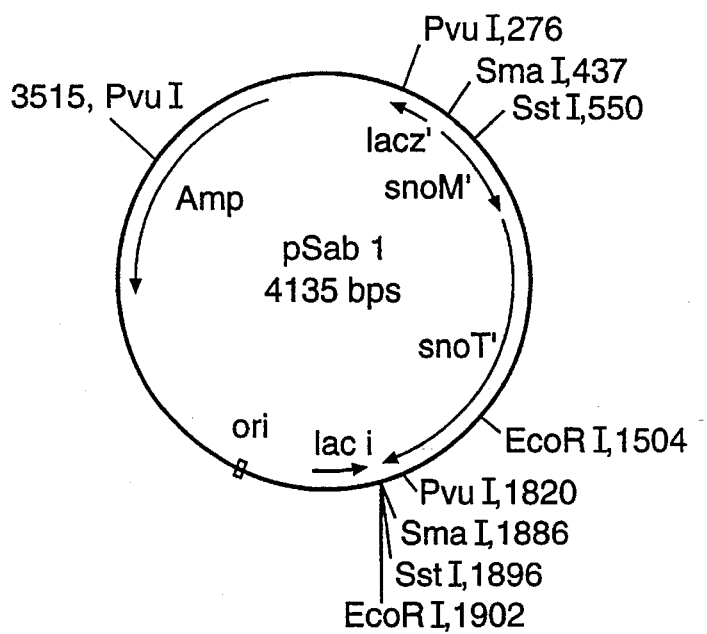
FIG. 3B
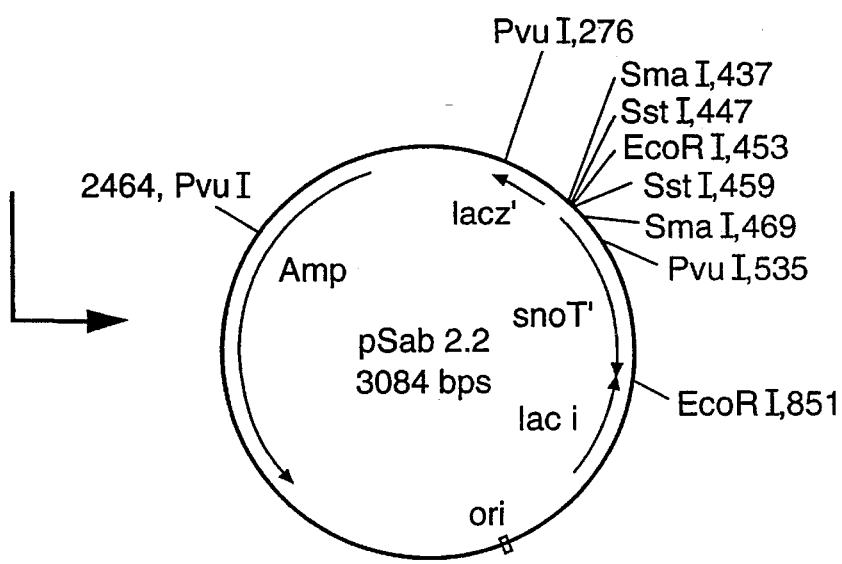

```
     BamHI                .         Smal
   1 GGATCCACAGTGTGCGCATACCGCCCGGGCAGGCCAAGTACGTCACCTGCGTCCG    55
       I  H  S  V  R  I  P  P  G  Q  A  K  Y  V  T  C  V  R
       snoM (C-TERMINAL)

56 CGGGGCGCTGCGCGACCTCGTGGTGGACCTGCGGATCGGCTCCCCGACCTTCGGC   110
      G  A  L  R  D  L  V  V  D  L  R  I  G  S  P  T  F  G

111 GAGCACCAGGTCAGCGAACTGGACGCGAGCTCCGGCAGGTCCGTCTACGTCCCCG   165
      E  H  Q  V  S  E  L  D  A  S  S  G  R  S  V  Y  V  P  E

166 AGGGCGTGGGCCACGGATTCCTGGCGCTCACCGACGACGCCTGCATCTGCTACGT   220
       G  V  G  H  G  F  L  A  L  T  D  D  A  C  I  C  Y  V

221 CGTCTCCACCGCGTACGTGCCGGGCACCCAGATCGACATCAACCCGCTCGATCCG   275
      V  S  T  A  Y  V  P  G  T  Q  I  D  I  N  P  L  D  P

276 GATCTCGCGCTGCCCTGGAACTGCCCGGAGACGCCCCTCATCTCGGACAAGGACG   330
      D  L  A  L  P  W  N  C  P  E  T  P  L  I  S  D  K  D  A

331 CGAAGGCGCCGACCGTGGCCGAGGCCGTACGGGCAGACCTCCTGCCCCGATTCAG   385
      K  A  P  T  V  A  E  A  V  R  A  D  L  L  P  R  F  S

386 CAAGGCGGGAACACCGTGAGAATGCTCTTCGTGGCGGCGGGCAGCCCGGCGACGG   440
      K  A  G  T  P  OPAL        M  A  A  G  S  P  A  T  V
                                 START snoT 441 TGTTCGCCCTGGCCCCGCTGGCCACCGCCGCCCGCAACGCGGGTCACCAGGTCGT   495
      F  A  L  A  P  L  A  T  A  A  R  N  A  G  H  Q  V  V 496 CATGGCCGCGAACGACGACATGGTTCCGGTCATCACCGCCTCGGGCCTGCCGGGC   550
      M  A  A  N  D  D  M  V  P  V  I  T  A  S  G  L  P  G 551 ATCGCGACCACCGATCTGCCGATCCGGCACTTCATCACCACGGACCGGGCCGGCA   605
      I  A  T  T  D  L  P  I  R  H  F  I  T  T  D  R  A  G  N 606 ACCCCGAGGAGATCCCCTCCGATCCGGTCGAGCAGGCGCTCTTCACCGGGCGCTG   660
       P  E  E  I  P  S  D  P  V  E  Q  A  L  F  T  G  R  W 661 GTTCGCGCGCATGGCCGCCTCCAGCCTGCCGCGGATGCTTGAGTTCTGCCGCGCC   715
      F  A  R  M  A  A  S  S  L  P  R  M  L  E  F  C  R  A
```

FIG. 4a

```
716  TGGCGGCCCGACCTGATCGTCGGCGGCACGATGAGCTACGTCGCCCCGCTGCTGG  770
     W  R  P  D  L  I  V  G  G  T  M  S  Y  V  A  P  L  L  A

771  CCCTGCACCTCGGCGTGCCGCATGTGCGCCAGACCTGGGACGCCATCGAGGCCGA  825
     L  H  L  G  V  P  H  V  R  Q  T  W  D  A  I  E  A  D

826  CGGCATCCATCCCGGCGCGGACGCCGAACTCCGTCCGGAACTCGCGGAGTTCGAC  880
     G  I  H  P  G  A  D  A  E  L  R  P  E  L  A  E  F  D

881  CTCGACCGGCTGCCCTTACCCGATGTGTTCGTGGACATCTGCCCGCCGAGCCTGC  935
     L  D  R  L  P  L  P  D  V  F  V  D  I  C  P  P  S  L  R

936  GGCCGGCCGGCGCCGCCCCGGCCCAGCCGATGCGGTACGTCCCGGCCAACGCCCA  990
     P  A  G  A  A  P  A  Q  P  M  R  Y  V  P  A  N  A  Q

991  GCGGCGGCTGGAGCCCTGGATGTACCGCCGGGGCGAGCGCCGCCGCGTCCTGGTG 1045
     R  R  L  E  P  W  M  Y  R  R  G  E  R  R  R  V  L  V
                                                   . EcoRI  .
1046 ACGTCCGGGAGCCGGGTCGCCAAGGAGAGCTACGAGAAGAACTTCGAATTCCTGC 1100
     T  S  G  S  R  V  A  K  E  S  Y  D  K  N  F  E  F  L  R

1101 GCGGCCTCGCCAAGGACGTCGCCGCCTGGGACGTCGAGCTGATCGTCGCCGCGCC 1155
     G  L  A  K  D  V  A  A  W  D  V  E  L  I  V  A  A  P

1556 GGAAGCGGTCGCCGACGCCCTGCACGACGAACTGCCGGGCATCCGGGCCGGCTGG 1210
     E  A  V  A  D  A  L  H  D  E  L  P  G  I  R  A  G  W

1211 GCACCGCTCGACGTGGTGGCGCCCACCTGCGATGTGCTCGTGCACCACGGGGGCG 1265
     A  P  L  D  V  V  A  P  T  C  D  V  L  V  H  H  G  G

1266 GCGTCAGCACCCTGACCGGGCTGAACGCCGGTGTGCCCCAACTGCTCATTCCGCG 1320
     V  S  T  L  T  G  L  N  A  G  V  P  Q  L  L  I  P  R

1321 GGGCGCCGTGCTGGAGAAGCCGGCCCTTCGCGTCGCCGATCACGGGGCAGCGATC 1375
     G  A  V  L  E  K  P  A  L  R  V  A  D  H  G  A  A  I

1376 ACGCTGCTGCCCGGCGAGGACGCGGCCGACGCGATCGCAGACTCCTGTCAGGAAC 1430
     T  L  L  P  G  E  D  A  A  D  A  I  A  D  S  C  Q  E  L
                                              . SmaI  .
1431 TGCTGTCCAAGGACACCTACGGCGAGCGGGCCCGCGAACTCTCCCGGGAGATCGC 1485
```

*FIG. 4b*

1486 CGCCATGCCCTCGCCCGCGAGCGTGGTCGACGCGCTCGAACCGGCATGAATACAC 1540
     A  M  P  S  P  A  S  V  V  D  A  L  E  P  A  OPAL

1541 GAAACCGAGAGGACCTCTCGATGAAGGCTCTGGTGCTCGCCGGCGGATCTGGTAC 1595
                     M  K  A  L  V  L  A  G  G  S  G  T
                     START snoD 1596 CCGCCTGCGGCCTTTCAGTTATTCGATGCCCAAACAACTGATCCCCATCGCCAAC 1650
     R  L  R  P  F  S  Y  S  M  P  K  Q  L  I  P  I  A  N 1651 ACACCCGTGCTGGTGCATGTGCTGAACGCCGTCCGGGAGCTGGGCGTGACCGAGG 1705
     T  P  V  L  V  H  V  L  N  A  V  R  E  L  G  V  T  E  V 1706 TCGGCGTCATCGTCGGCAACCGCGGCCCCGAGATCGAGGCCGTGCTCGGCGACGG 1760
      G  V  I  V  G  L  R  G  P  E  I  E  A  V  L  G  D  G 1761 TGCCCGGTTCGACGTGCGCATCACCTACATCCCCCAGGACGCACCGCGCGGACTG 1815
      A  R  F  D  V  R  I  T  Y  I  P  Q  D  A  P  R  G  L 1816 GCCCACACCGTGTCCATCGCCCGCGGCTTCCTCGGCGACGACGACTTCGTGATGT 1870
      A  H  T  V  S  I  A  R  G  F  L  G  D  D  D  F  V  M  Y 1871 ACCTCGGCGACAACATGCTGCCCGACGGAGTCACCGAGATCGCCGAGGAGTTCAC 1925
      L  G  D  N  M  L  P  D  G  V  T  E  I  A  E  E  F  T 1926 CCGGCAGCGCCCGGCCGCCCAGGTCGTCGTGCACAAGGTCCCCGACCCGCGCTCC 1980
      R  Q  R  P  A  A  Q  V  V  V  H  K  V  P  D  P  R  S 1981 TTCGGCGTCGCCGAACTCGGCCCCGACGGGGAGGTGCTGCGCCTGGTGGAGAAGC 2035
      F  G  V  A  E  L  G  P  D  G  E  V  L  R  L  V  E  K  P 2036 CGTGGCAGCCGCGCAGCGACATGGCCCTGATCGGGGTCTACTTCTTCACCGCCGC 2090
      W  Q  P  R  S  D  M  A  L  I  G  V  Y  F  F  T  A  A 2091 CATCCACCAGGCGGTGGCGGCCATCTCGCCCAGCAGCCGCGGCGAACTGGAGATC 2145
      I  H  Q  A  V  A  A  I  S  P  S  S  R  G  E  L  E  I 2146 ACCGACGCCGTCCAGTGGTTGGTCACCTCCGGCGCGGACGTGCGCGCCAGCCTCT 2200
      T  D  A  V  Q  W  L  V  T  S  G  A  D  V  R  A  S  L  Y 2201 ACGACGGCTACTGGAAGGACACCGGGAGGGTCGAGGACGTCCTTGAGTGCAACAG 2255
      D  G  Y  W  K  D  T  G  R  V  E  D  V  L  E  C  N  S

*FIG. 4c*

2256 CCACCTCCTGGACGGCCTGACCCCGCGCGTCGACGGACAGGTCGACGCCGACAGC 2310
     H   L   L   D   G   L   T   P   R   V   D   G   Q   V   D   A   D   S

2311 GTGCTCGTCGGCCGGGTCGTGATCGAGGCGGGGGCGCGCATCGTGCGGTCGCGGG 2365
     V   L   V   G   R   V   V   I   E   A   G   A   R   I   V   R   S   R   V

2366 TCGAGGGCCCGGCGATCATCGGCGCGGGCACGGTCCTTCAGGACAGCCAGGTGGG 2420
       E   G   P   A   I   I   G   A   G   T   V   L   Q   D   S   Q   V   G

2421 CCCGCACACCTCCATCGGGCGGGACTGCACGGTGACGGACAGCCGGCTGGAGGGC 2475
       P   H   T   S   I   G   R   D   C   T   V   T   D   S   R   L   E   G

2476 TCCATCGCCCTGGACGAGGCGTCGGTCACCGGCGTGCGCGGCCTGCGCAACTCGC 2530
       S   I   A   L   D   E   A   S   V   T   G   V   R   G   L   R   N   S   L

2531 TGATCGGGCGCGCCGCGTCCGTCGGCACCACCGGCCCCGGCACGGGCCATCACTG 2585
       I   G   R   A   A   S   V   G   T   T   G   P   G   T   G   H   H   C

BamHI
2586 CCTGGTCGTCGGAGACCACACCCGAGTGGAGGTCGCGGCATGAGGATCC        2634
       L   V   V   G   D   H   T   R   V   E   V   A   A  OPAL

*FIG. 4d*

SECONDARY-METABOLITE BIOSYNTHESIS GENES FROM ACTINOMYCETES, METHOD OF ISOLATING THEM AND THEIR USE

The invention concerns secondary-metabolite biosynthesis genes from actinomycetes, a method of isolating secondary-metabolite and, in particular, 6-deoxy-sugar biosynthesis genes, from actinomycetes using the gene probes strD, strE, strL and strM gene probes from *Streptomyces griseus* DSM40236, and structurally related genes, as gene probes for detecting the genes snoT (coding for amphotheronolide B-dTDP-D-mycosaminyl transferase), snoD (coding for dTDP-D-glucose synthase) and snoM (coding for dTDP-4-keto-6-deoxy-D-glucose isomerase), or one or more secondary-metabolite biosynthesis genes from actinomycetes. The invention also concerns the use of secondary-metabolite biosynthesis genes thus isolated.

One of the fields of activity in recombinant DNA technology is the isolation of particular genes directly out of the genome. In order to detect the gene to be isolated, gene probes can, for example, be employed which bind specifically to the desired DNA sequence. In this way, this latter sequence can be "fished out" (detected by screening) from a large number of other sequences.

Secondary-metabolite biosynthesis genes (genes for antibiotics, anthelmintics, antifungal substances, enzyme inhibitors, dyes, etc.) which have hitherto been investigated are present adjacent to each other within a unit on the bacterial chromosome or on very large plasmids. This applies particularly to streptomycetes and other actinomycetes [C. L. Hershberger et al. (1989), Genetics and Molecular Biology of Industrial Microorganisms, Am. Soc. for Microbiol., Washington, D.C. 20005, pp. 35–39, p. 58, pp. 61–67, pp. 147–155].

Thus, in actinomycetes, genes for the biosynthesis of 6-deoxy sugars, for example, are located on the genome in close proximity to other secondary-metabolite biosynthesis genes [J. F. Martin et al. (1989), Ann. Rev. Microbiol 43: 173–206].

In addition to this, it is known that a multiplicity of secondary metabolites from actinomycetes contain 6-deoxy sugar residues. Examples are, inter alia, aminoglycosides (e.g. spectinomycin, kasugamycin and streptomycin), polyenes (e.g. amphotericin A and B, and nystatin), macrolides (e.g. tylosin, erythromycin and avermectin), nucleosides (e.g. antibiotic A201A) and anthracyclines (e.g. daunorubicin and cytorhodin A) and glycopeptides (e.g. vancomycin) and isochromanequinones (e.g. granaticin).

The pathway for the biosynthesis of a 6-deoxy sugar residue of streptomycin, the L-dihydrostreptose residue, is depicted in FIG. 1.

Until recently, there were still no sequence data available for actinomycetes genes or enzymes which are involved in the biosynthesis of 6-deoxy sugars. As a result of cloning and analyzing the genes for the biosynthesis of streptomycin, it was possible to isolate and identify the genes for the 6-deoxy sugar component, L-dihydrostreptose: strD (dTDP-D-glucose synthase), strE (dTDP-D-glucose 4,6-dehydratase), strM (dTDP-4-keto-L-rhamnose 3,5-epimerase) and strL (dTDP-L-dihydrostreptose synthase) from *Streptomyces griseus* DSM40236.

The use of heterologous gene probes, i.e. gene probes which are employed for screening in another species or for isolating genes within another biosynthesis pathway, for the isolation of secondary-metabolite biosynthesis genes has thus far been limited to only a few genes (e.g. polyketide synthetase genes) [Nature (1987) 325: 818–821]. Using these polyketide synthetase gene probes, it is only possible to detect compounds which are formed via the polyketide synthetase biosynthesis pathway [C. L. Hershberger et al. (1989), Genetics and Molecular Biology of Industrial Microorganisms, Am. Soc. for Microbiol., Washington, D.C. 20005, pp. 76–78; S. L. Otten et al., J. Bacteriol. 172, No. 6 (1990), pp. 3427–3434], and not functionally different genes, such as aminoglycoside biosynthesis genes, for example.

It has now been found, surprisingly, that one or more gene probes from the strD, strE, strL or strM group of genes from *Streptomyces griseus* DSM40236, and structurally related genes, are suitable for use as gene probes for detecting the genes snoT (encoding amphotheronolide B-dTDP-D-mycosaminyl transferase), snoD (encoding dTDP-D-glucose synthase) and snoM (encoding dTDP-4-keto-6-deoxy-D-glucose isomerase), or one or more secondary-metabolite biosynthesis genes from actinomycetes. The screening for the secondary-metabolite biosynthesis genes does not depend on the chemical structure of the secondary metabolites. The only prerequisite is that they possess 6-deoxy sugar residues.

The invention therefore discloses:

The complete DNA sequence of snoT and snoD as well as part of the DNA sequence of snoM.

The complete amino acid sequence of snoT and snoD as well as part of the amino acid sequence of snoM.

A method for isolating secondary-metabolite biosynthesis genes from actinomycetes, wherein one or more genes from the strD, strE, strL or strM group of genes from *Streptomyces griseus* DSM40236, and structurally related genes, are used as gene probes for detecting the genes snoT (encoding amphotheronolide B-dTDP-D-mycosaminyl transferase), snoD (encoding dTDP-D-glucose synthase) and snoM (encoding dTDP-4-keto-6-deoxy-D-glucose isomerase), or one or more secondary-metabolite biosynthesis genes from actinomycetes.

The use of the isolated secondary-metabolite biosynthesis genes for forming hybrid natural substances.

The use of the isolated secondary-metabolite biosynthesis genes for increasing the yield of secondary metabolites in actinomycetes.

The use of the isolated secondary-metabolite biosynthesis genes for isolating biosynthesis enzymes.

The use of the isolated secondary-metabolite biosynthesis genes for biotransformation in actinomycetes.

The use of the isolated secondary-metabolite biosynthesis genes for screening secondary-metabolite producers.

BRIEF DESCRIPTION OF THE DRAWINGS

FIG. 3b shows restriction maps of plasmids pSab1, pSab2.1, and pSab2.2.

FIGS. 4a, 4b, 4c and 4d show the nucleotide sequence and deduced amino acid sequences of the SnoM (dTDP-4-keto- 6-deoxy-D-glucose 3,4-isomerase), Snot (amphotheronolide B-dTDP-D-micosaminyl transferase) and SnoD (dTDP-D-glucose synthase) genes from the amphotericin producer *S. nodosus* DSM 40109.

Figure 1:
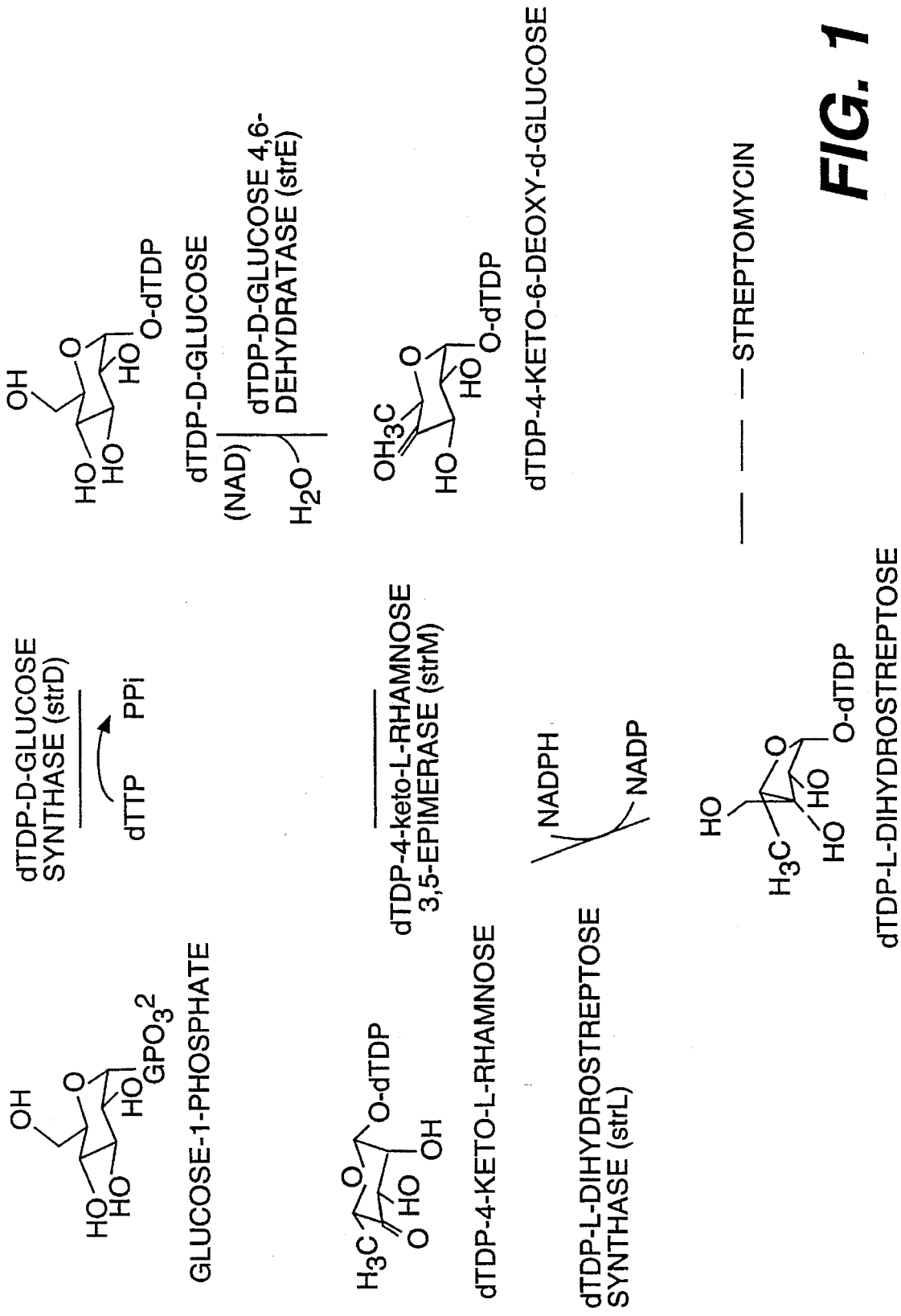
FIG. 1 shows the pathway for the biosynthesis of the L-dihydro-streptose residue of streptomycin in *S.griseus* DSM 40236.
Figure 2A:
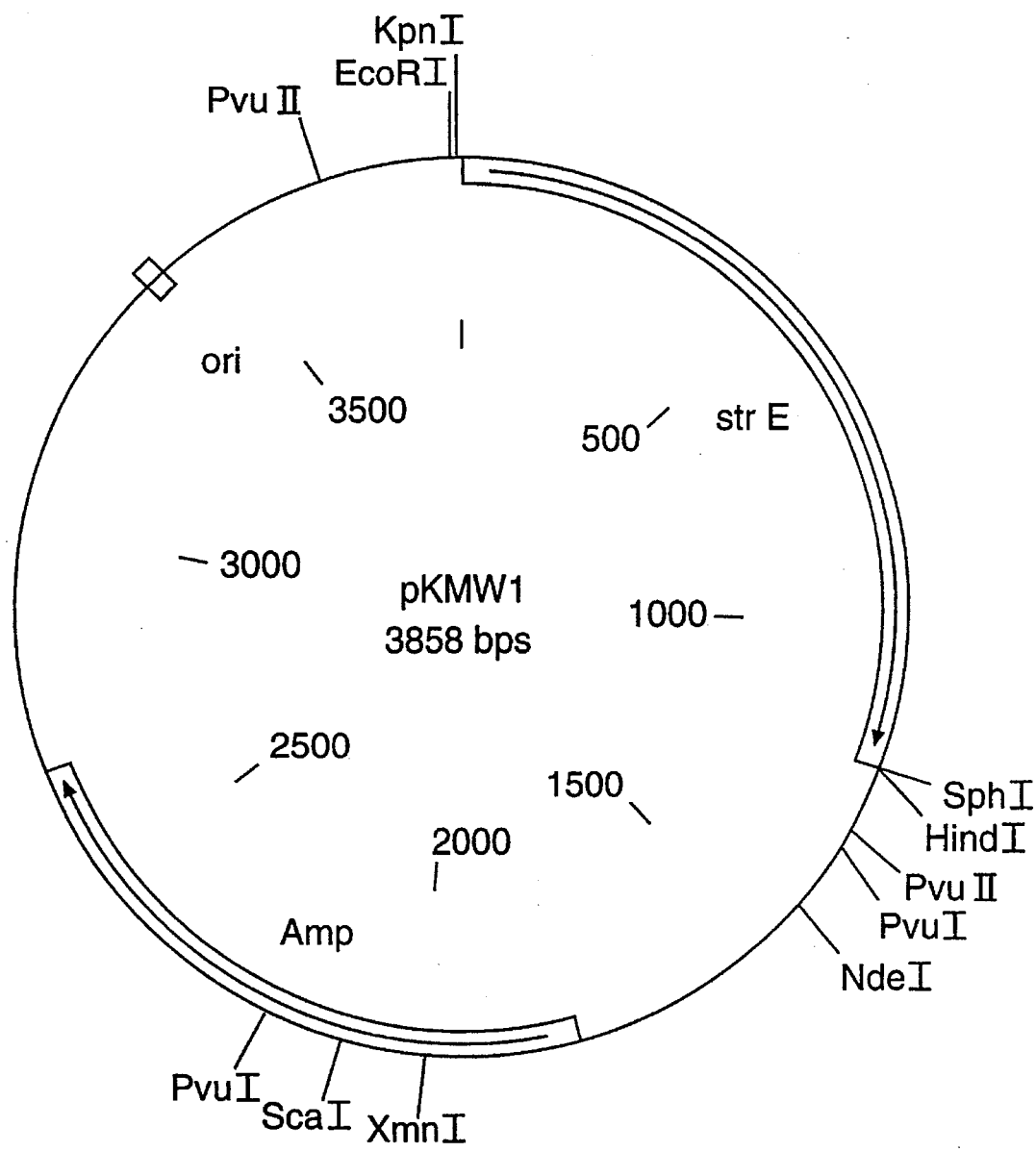
FIG. 2a shows a restriction map of the plasmid pJDM 1018.
Figure 2B:
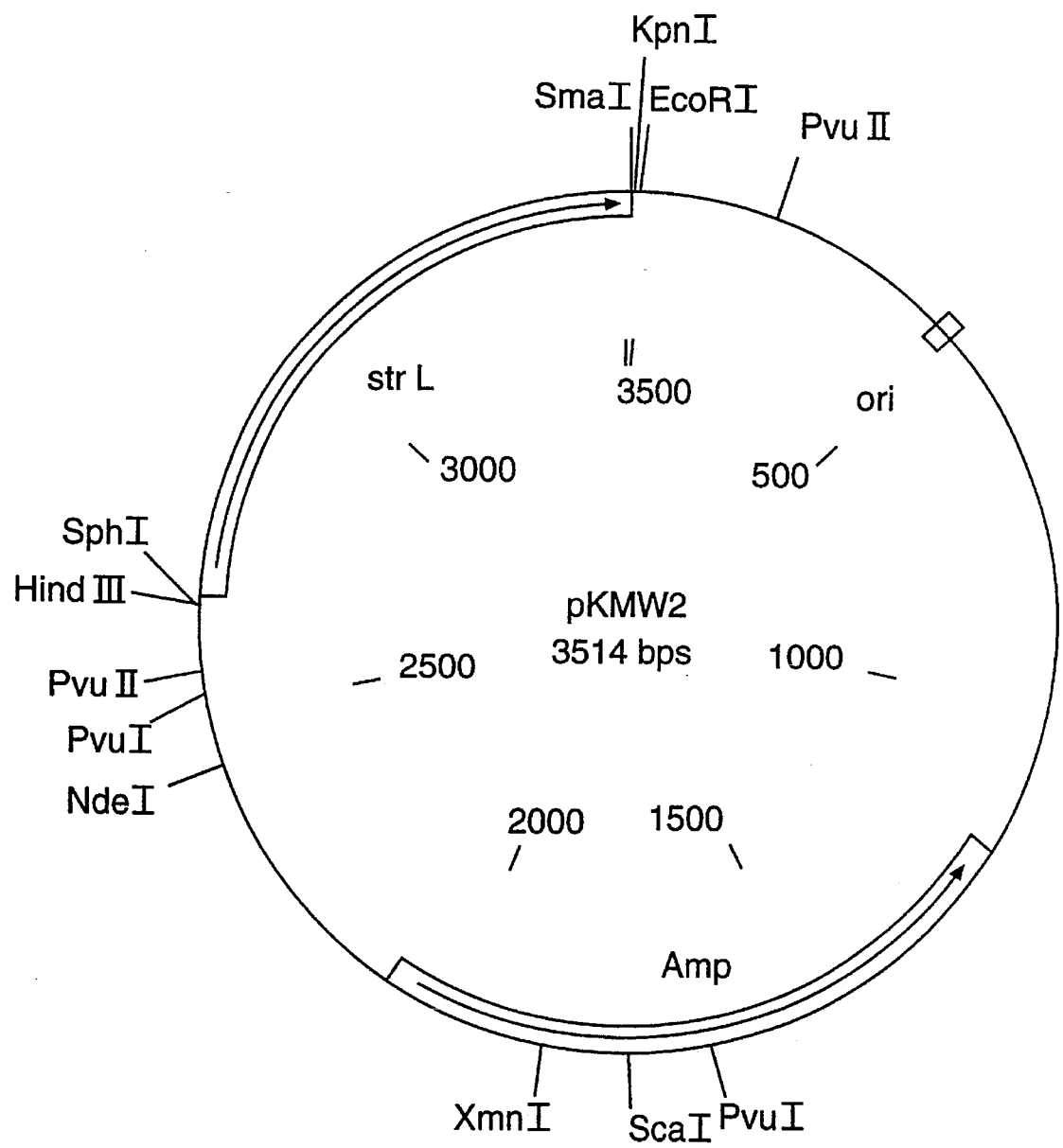
FIG. 2b shows a restriction map of the plasmid pKMW1.
Figure 2C:
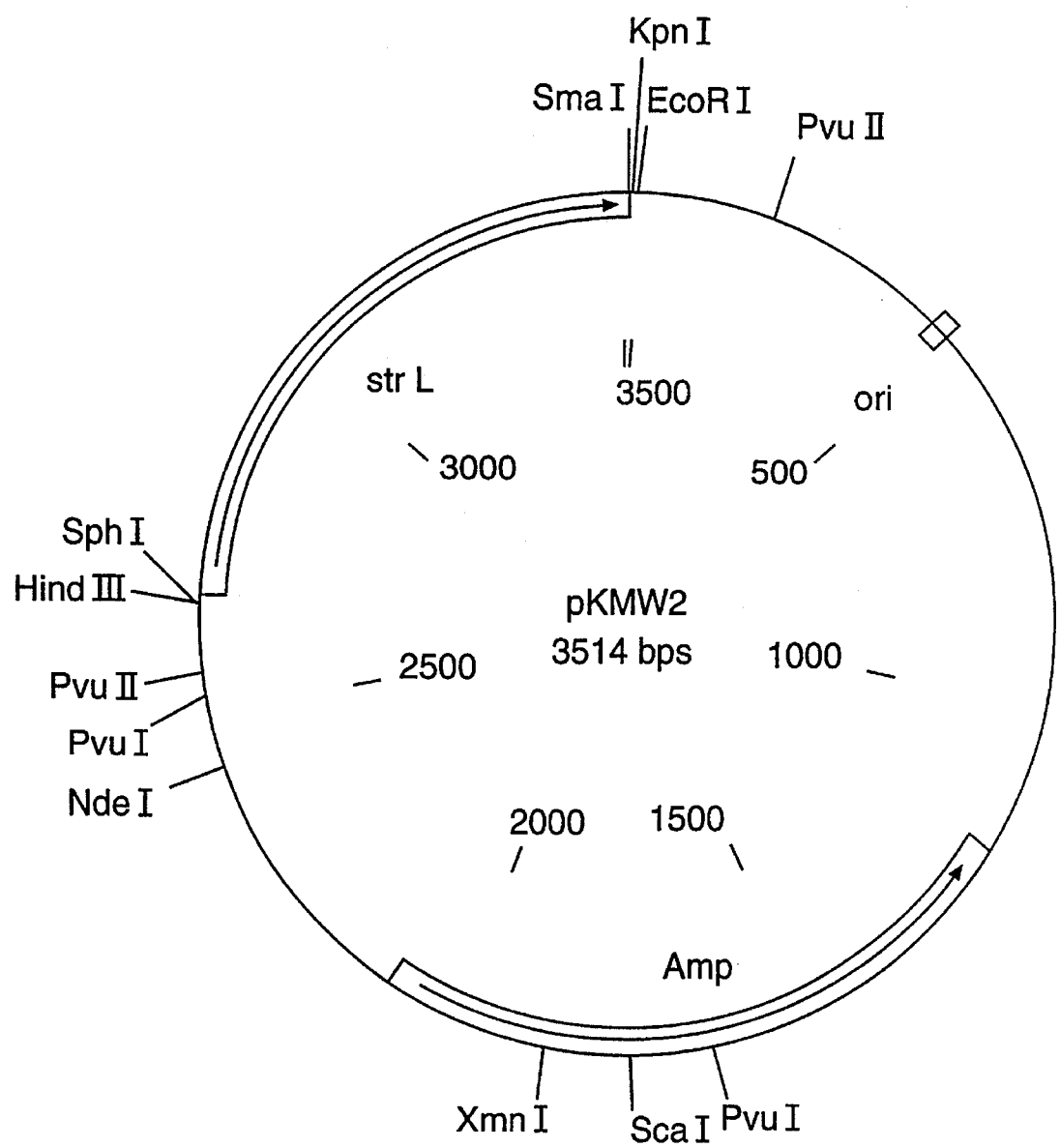
FIG. 2c shows a restriction map of the plasmid pKMW2.
Figure 2D:
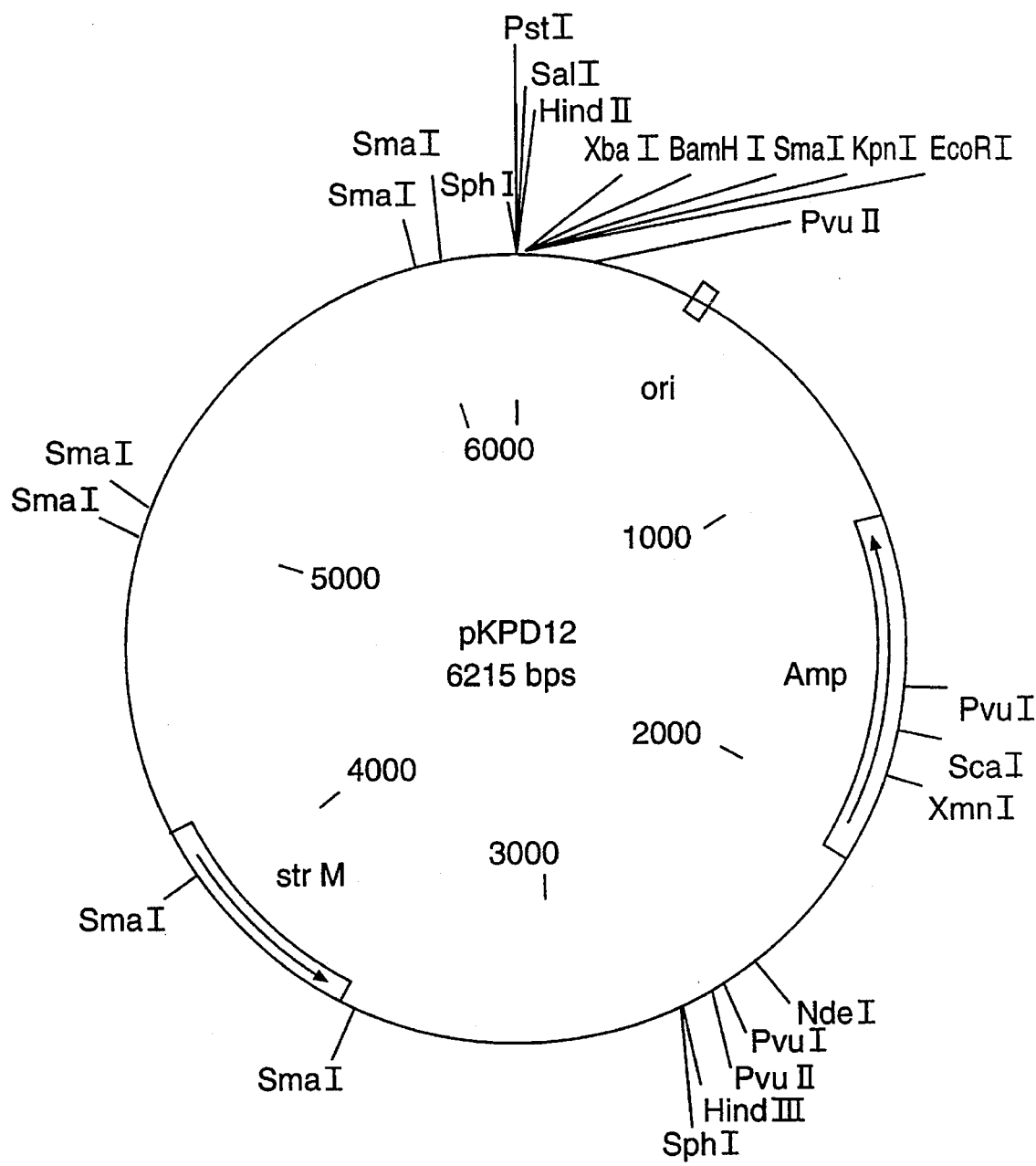
FIG. 2d shows a restriction map of the plasmid pKPD12.

The invention is described in detail below. In addition, the invention is determined by the content of the claims.

All methods involving recombinant DNA technology were, unless otherwise indicated, taken from J. Sambrook et al. (Molecular Cloning; A laboratory manual [2nd edition] 1989; Cold Spring Harbor Laboratory Press, New York, U.S.A.).

The gene probes strD, strE, strL and strM, which are required for the screening, are deposited, in the *E. coli* strains FH-L 8138 (strD), FH-L 8154 (strE), FH-L 8158 (strL) and FH-L 8159 (strM), with the Deutsche Sammlung von Mikroorganismen und Zellkulturen GmbH (German collection of microorganisms and cell cultures) (DSM), 3300 Braunschweig, Mascheroder Weg 1b, Germany, on 30.08.1991 under the following numbers DSM6681 (FH-L 8138), DSM6682 (FH-L 8154), DSM6683 (FH-L 8158) and DSM6684 (FH-L 8159). The plasmids pJDM1018 (strD), pKMW1 (strE), pKMW2 (strL) and pKPD12 (strM) [see FIGS. 2a to 2d, respectively] are isolated from the abovementioned *E. coli* strains using the boiling method and by alkaline lysis (J. Sambrook et al. 1989).

The plasmids pJDM1018 (strD), from *E. coli* DSM6681, and pKMW1 (strE), from *E. coli* DSM6682, are cut with the restriction enzymes EcoRI and HindIII. A 0.7 kb EcoRI/HindIII fragment of the plasmid pJDM1018 and a 1.2 kb EcoRI/HindIII fragment of the plasmid pKMW1 are isolated and provided with $^{32}$P-labeled deoxynucleotides using so-called "nick translation". These radioactively labeled fragments are designated below as gene probes strD and strE, respectively.

A 0.8 kb EcoRI-HindIII fragment is isolated from the plasmid pKMW2 (strL) from *E. coli* DSM6683, as is a 0.5 kb SmaI fragment from the plasmid pKPD12 (strM) from *E. coli* DSM6684, and these fragments are then radioactively labeled and employed as gene probe strL and strM, respectively.

In principle, any other extended, truncated or modified fragment or synthetic oligodeoxynucleotide can be used as a gene probe in place of the abovementioned gene probes as long as it hybridizes with the gene for the biosynthesis of deoxysugar residues.

The procedure for isolating one or more secondary-metabolite biosynthesis genes is as follows:

The total DNA of any one of the actinomycetes strains listed in Table 1 can be isolated, cleaved using the restriction endonuclease BamHI, and other restriction enzymes, and fractionated by gel chromatography. The total DNA of *Streptomyces nodosus* DSM40109 is preferably used.

Hybridization with 6-deoxy sugar gene probes, preferably with the strD gene probe, then takes place. The DNA fragments, preferably those of 1.5–3 kb in size, which hybridize with the 6-deoxy sugar gene probes, preferably with the strD gene probe from *S. nodosus* DSM40109, are isolated from the gel and ligated into a suitable vector and then cloned in a microorganism which is compatible for the vector.

The vectors pUC18 (Boehringer Mannheim, Germany) and pEB15 from *S. coelicolor* Müller DSM4914, and the host strains *E. coli* K12 and *S. lividans* 66, are preferably employed. *E. coli* DH5alpha (Gibco BRL, Eggenstein, Germany) and *S. sp* DSM40434 are very preferably used.

The clones containing plasmid DNA are isolated and hybridized with the respective gene probe, preferably with the strD probe from *S. griseus* DSM40236. In this context, pools of ten can in each case be used, which pools can then be split into the individual clones if hybridization occurs, with the plasmids being isolated and subjected once again to hybridization. A plasmid which hybridizes with a gene probe is cleaved by restriction enzymes. Hybridizing restriction fragments, preferably those which hybridize with the strD gene probe from *S. nodosus* DSM40109, are isolated and subcloned into a vector, preferably pUC18, and into a host strain, preferably *E. coli* DH5alpha, and then examined by DNA sequence analysis.

If appropriate, that region of the cloned fragment which is to be sequenced can be delimited more closely by repeating the subcloning prior to the DNA sequence analysis, and subclones which are suitable for the sequencing can be identified by hybridization, preferably using the strD gene probe.

Preferably, the 2.6 kb BamHI fragment which is isolated from the total DNA of the amphotericin B-producer *S. nodosus* DSM40109, and which hybridizes with the strD probe, is cloned into the vector pEB15 in *S. sp.* DSM40434. The resultant plasmid pPS72.2 (see FIG. 3A) is cleaved with restriction enzymes, e.g. with SmaI-SstI, and the DNA fragments which are obtained are subcloned in pUC18 in *E. coli* DH5alpha, and sequenced.

Figure 3A:
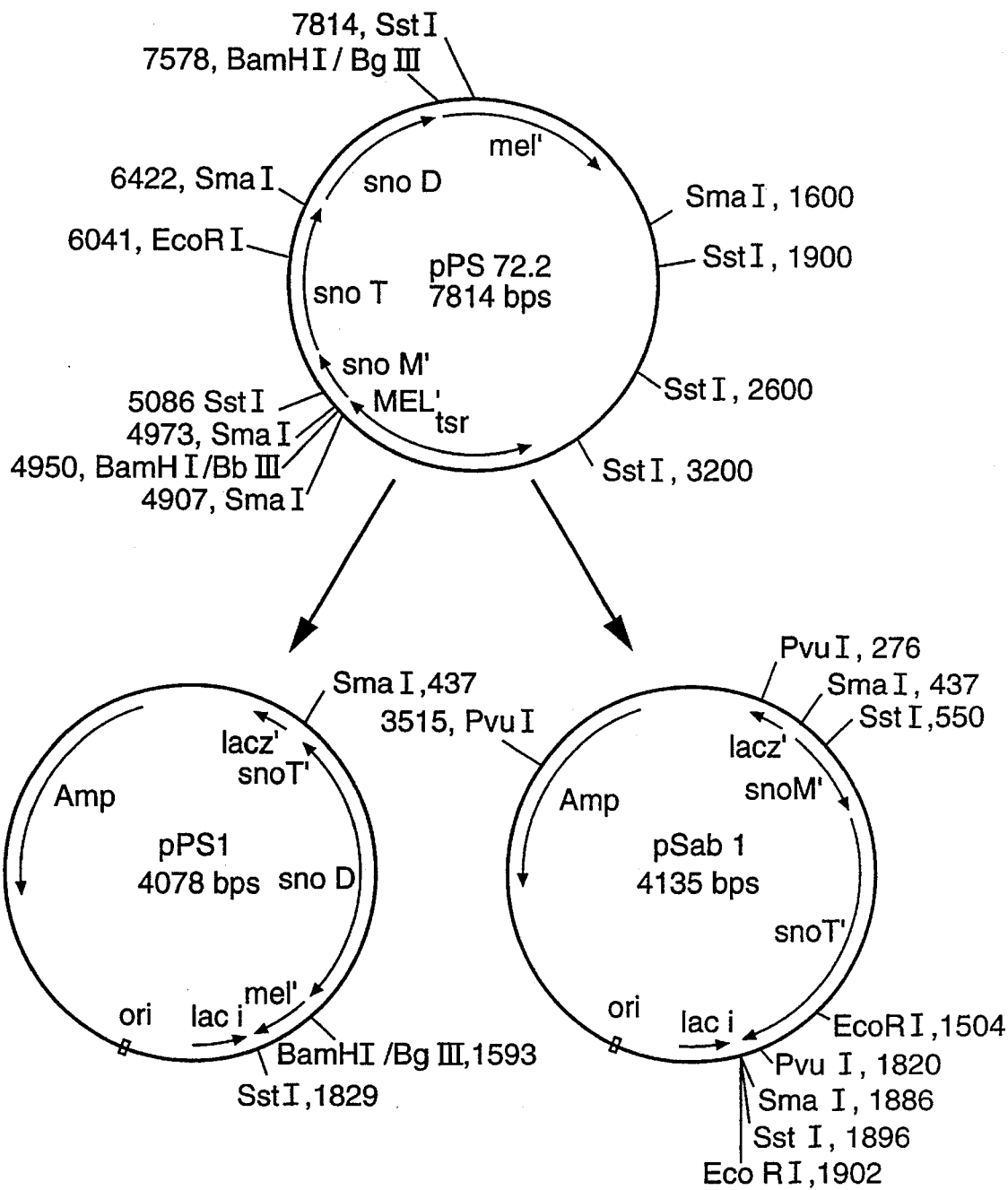
FIG. 3a shows restriction maps of plasmids pPS72.2, pPS1 and pSab1.
Figure 3C:
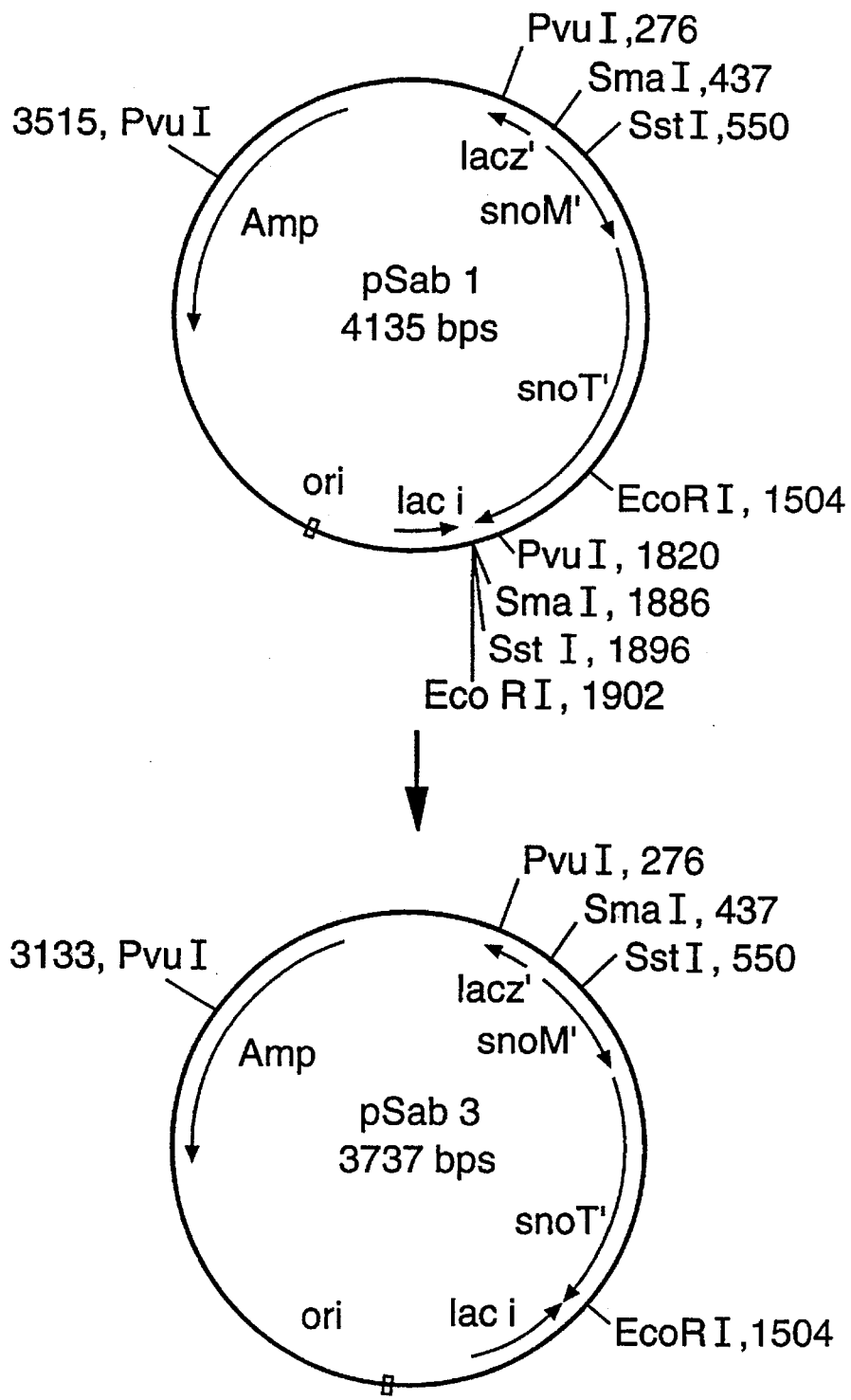
FIG. 3c shows restriction maps of pSab1 and pSab3.

For the subcloning, the abovementioned DNA fragments are isolated. Preferably, the 1.4 kb SmaI/SstI and the 1.45 kb SmaI fragments are isolated from the plasmid pPS72.2 and then subcloned into pUC18, resulting in the production of the plasmids pPS1 and PSab1 (FIG. 3A). Preferably, the 0.4 kb EcoRI fragment is isolated from plasmid pSab1 and cloned, in both possible orientations, into pUC18 in *E. coli* DH5alpha, resulting in the production of the plasmids pSab2.1 and pSab2.2 (see FIG. 3A); the 3.7 kb EcoRI fragment of plasmid pSab1 is isolated, religated and transformed into *E. coli* DH5alpha, resulting in the production of the plasmid pSab3 (see FIG. 3A).

The plasmids which contain a DNA fragment hybridizing with a gene probe are used for the DNA sequencing. Preferably, the 2.6 kb BamHI fragment of *S. nodosus* DSM40109, contained in plasmid pPS72.2, is sequenced completely and in both strand directions. Plasmid pPS72.2, and the plasmids pPS1, pSab1, pSab3, pSab2.1 and pSab2.2 derived from it, are preferably used for this purpose, once they have been isolated by alkaline lysis and purified by being subjected twice to cesium chloride gradient centrifugation.

The method of A. M. Maxam and W. Gilbert (1977) Proc. Natl. Acad. Sci. USA 74:560–564 or that of F. Sanger et al. (1977) Proc. Natl. Acad. Sci. USA (1977) 74:5463–5467, or a process derived from one of these methods, is employed for the DNA sequencing. The Promega fmol™ sequencing system, which operates in accordance with the method of Sanger (Serva, Heidelberg, Germany), is preferably used.

Suitable primers are either obtained from commercial sources (pUC reverse-sequencing and sequencing primers, Boehringer Mannheim, Germany) or else synthesized (see Table 2) as described in EP-A-0,368,244 (Example 16).

Open reading frames, or parts thereof, are recognized from the codon usage which is characteristic for streptomycetes (F. Wright et al. 1992, Gene 113:55–65) and from the presence of a start codon (ATG or GTG) and/or a stop codon (TAG, TGA or TAA). Amino acid sequences deduced from the DNA sequence are compared with the amino acid sequences of known gene products. The analysis of open reading frames is preferably carried out using the FASTA or TFASTA programs of the Database Searching Program, Version 7, of the GCG Package, Genetics Computer Group Inc. Wisconsin, U.S.A.). This then involves searching one or more of the SwissProt, NBRF-Protein (Pir), Genbank and/or EMBL databases for sequences which are similar to the open reading frame which has been identified. Conclusions are drawn with regard to the function of the relevant gene product from a comparison of its amino acid sequence with that of known proteins and comparison with the assumed pathway for the biosynthesis of dTDP-D-mycosamine (Juan-Francisco Martin, Biosynthesis of Polyene Macrolide Antibiotics; Ann. Rev. Microbiol. 1977, 31:13–38).

Alternatively, the DNA sequences can also be compared with known DNA sequences and corresponding reading frames.

The gene products which are designated snoM, snoT and snoD, and which encode dTDP-4-keto-6-deoxy-D-glucose 3,4-isomerase, B-dTDP-mycosaminyl transferase and dTDP-D-glucose synthase, are preferably identified.

Besides this, the identified snoM, snoT and snoD genes can be employed for detecting novel secondary metabolites containing 6-deoxy sugars.

All actinomycetes genes relating to the biosynthesis of 6-deoxy sugars, but particularly the L-dihydrostreptose biosynthesis genes strL and strM, and very preferably the genes strD and strE from *Streptomyces griseus* DSM40236, are suitable for use as gene probes for detecting novel secondary-metabolite and 6-deoxysugar biosynthesis genes in actinomycetes.

Instead of the strD, strE, strL and strM gene probes from *Streptomyces griseus* DSM40236, genes which are functionally and structurally similar, such as those from the hydroxystreptomycin producer *Streptomyces glaucescens* DSM40716, the candicidin producers *Streptomyces coelicolor* DSM40624 and *Streptoverticillium sp.* DSM40237, the perimycin producer *Streptomyces aminophilus* DSM40186, the pimaricin producer *Streptomyces sp.* DSM40357, the lucensomycin producer *Streptomyces lucensis* DSM40317, the rimocidin producer *Streptomyces rimosus* DSM40260, the levorin A2 producer *Streptomyces sp.* DSM40202, the lienomycin producer *Streptomyces lienomycini* ATCC43687, the monazomycin producer *Streptoverticillium mashuense* NRRL B-3352, the picromycin producers *Streptomyces felleus* DSM40130 and *Streptomyces olivaceus* DSM40702, the narbomycin producer *Streptomyces narbonensis* DSM40016, or the methymycin producers *Streptomyces venezuelae* ATCC15068 and ATCC15439, for example, may also be employed as probes which are specific for secondary metabolites.

The genes from the amphotericin B producer *Streptomyces nodosus* DSM40109, the nystatin producer *Streptomyces noursei* DSM40635, the rhodomycin producer *Streptomyces purpurascens* DSM2658 and the streptomycin producer *Streptomyces griseus* DSM40236 are preferably used.

In addition to this, the gene probes which are specific for secondary metabolites can be used for:

Forming Hybrid Natural Substances:

For this purpose, the said gene probes are used for the transfer of isolated genes into a different actinomycetes strain in order to cause this strain to synthesize a novel secondary metabolite. In this context, the 6-deoxy sugar biosynthesis genes and transferase genes, and other secondary-metabolite biosynthesis genes as well, are particularly suitable for use in the formation of novel hybrid natural substances.

Increasing the Yield of Secondary Metabolites in Actinomycetes:

In some actinomycetes strains, the activity of the enzymes for the biosynthesis of 6-deoxy sugars is limited by different factors. By means of cloning the 6-deoxy-sugar biosynthesis genes from an actinomycetes strain and then reintroducing the cloned gene into this strain at higher copy number, the yield of gene products, and thus the level of secondary-metabolite production, can be increased. This also applies to other cloned secondary-metabolite biosynthesis genes.

Isolating Biosynthesis Enzymes:

The chemical synthesis of 6-deoxy sugars is costly, since it requires sophisticated protective group technology. It is advantageous to use enzymes to synthesize the sugars in vitro without the need for protective groups. The preparation of the 6-deoxy-sugar biosynthesis enzymes for the enzymes synthesis is facilitated if the above-described 6-deoxy-sugar biosynthesis genes are present at increased copy number.

Carrying Out Biotransformations in Actinomycetes:

The glycosylation of a secondary-metabolite precursor (natural aglycone) in an actinomycetes strain is brought about by the products of 6-deoxy-sugar biosynthesis genes and transferase genes. Other compounds (foreign aglycones) can be fed to a strain and be glycosylated. By means of self-cloning 6-deoxy-sugar biosynthesis genes and transferase genes, i.e. cloning the genes from a strain and reintroducing them into the same strain at a high copy number, the rate at which a foreign (fed) aglycone is glycosylated is then increased.

Identifying Other Genes:

As already mentioned in the introduction, gene probes can also be used to isolate genes which are structurally and functionally novel and for which no previous sequence homology is known.

Screening Secondary-Metabolite Producers:

Producers of secondary metabolites which contain 6-deoxy sugars are identified with the aid of the above-mentioned gene probes. This leads in turn to the isolation of novel secondary metabolites.

EXAMPLE

1. Cultivation of *E. coli* Strains, Preparation of Plasmid DNA and Isolation of DNA Fragments The strains *E. coli* DSM6681 (contains the strD gene on plasmid pJDM1018) and *E. coli* DSM6682 (contains the strE gene on plasmid pKMW1) are in each case cultivated at 37° C. for 16 hours in 1 liter of Luria Bertani (LB) medium (1% Bactotryptone, 0.5% Bactoyeast extract, 1% sodium chloride, pH 7.0) which is supplemented with 100 µg/ml ampicillin after auto-claving. The plasmids pJDM1018 and pKMW1 are isolated from these strains by alkaline lysis and are subsequently subjected twice to cesium chloride density gradient centrifugation, as described in J. Sambrook et al. (1989).

5 U each of EcoRI and HindIII (from Boehringer Mannheim, Mannheim, Germany) are added in each case to 10 µg of the isolated plasmid DNA in 10 mM Tris-HCl, pH 8.0, 5 mM MgCl$_2$, 100 mM NaCl, 1 mM mercaptoethanol, and the mixtures are then incubated at 37° C. for 2 hours.

The cleaved plasmid DNA is in each case loaded onto a horizontal 0.8% agarose gel and fractionated by electrophoresis (J. Sambrook et al. 1989).

Using a scalpel, a narrow pocket is cut out of the agarose gel immediately in front of the 0.7 kb and 1.2 kb, respectively, EcoRI/HindIII fragments of the two plasmids pJDM1018 and pKMW1, and then filled with TBE buffer (0.045M Tris-borate, 0.001M EDTA, pH 8.0). The DNA fragments are transferred electrophoretically into the pockets as described in T. Maniatis et al. (1989). The buffer is then removed from the pockets and extracted with phenol/chloroform and chloroform/isoamyl alcohol, and the DNA is subsequently precipitated with absolute ethanol and washed with 70% ethanol; the DNA sediment which has been obtained is then dried and dissolved in 50 µl TE buffer (10 mM Tris-HCl, 0.1 mM EDTA, pH 8.0).

2. Preparation of the strD and strE Gene Probes

5 µg of the DNA fragments which derived from plasmids pJDM1018 and pKMW1 (strD gene and strE gene, respectively), and which were prepared in accordance with point 1, are incubated at 15° C. for 35 minutes in 50 mM Tris-HCl, pH 7.5, 10 mM MgSO$_4$, 0.1 mM dithiothreitol, 50 µg/ml bovine serum albumin (fraction V, from Sigma, Deisenhofen, Germany) together with 5 U $E.$ $coli$ DNA polymerase I (nick translation grade, Boehringer Mannheim, Germany) and 50 µM dATP and 50 µM dTTP, and 40µ Ci each of [$\alpha^{-32P}$]-dCTP and [$\alpha^{-32P}$]-dGTP (3000 Ci/mmol; from DuPont de Nemours, NEN Division, Dreieich, Germany). The reaction is stopped by adding 0.02 mM EDTA, pH 8.0, and heating at 65° C. for 10 minutes. Unincorporated radionucleotides are separated off, as described in J. Sambrook (1989), by gel filtration in TE buffer (10 mM Tris-HCl, 0.1M EDTA, pH 8.0) on a 0.5×10 cm Sephadex G15 column.

The radioactively labeled 0.7 kb and 1.2 kb EcoRI/HindIII fragments, deriving from plasmids pJDM1018 and pKMW1, respectively, and having been purified by gel filtration, are designated the strD and strE gene probes, respectively; immediately prior to use, they are denatured at room temperature for 5 minutes with 0.3M sodium hydroxide solution, then neutralized with 0.3M HCl and 0.3 Tris-HCl pH 7.0, boiled for 5 minutes and immediately cooled in ice water.

3. Isolation, Cleavage and Fractionation by Gel Electrophoresis of Streptomycetes Total DNA The streptomycetes strains $S.$ $nodosus$ DSM40109 and NRRLB-2371, $S.$ $noursei$ DSM40635 and NRRLB-1714, $S.$ $aminophilus$ DSM40186, $S.$ $lucensis$ DSM40317, $S.$ $venezulae$ NRRLB-2447, $S.$ $narbonensis$ DSM40016, $S.$ $griseus$ DSM40236 and $S.$ $glaucescens$ DSM40716 are cultivated at 30° C. for three days in 100 ml CASO broth (casein peptone-soya bean meal-peptone broth, from Merck, Darmstadt, Germany). The total DNA of these strains is isolated by the method described in D. A. Hopwood et al. (1985), Genetic manipulation of Streptomyces; A laboratory manual; The John Innes Foundation, Norwich, England.

The genomic DNA of $S.$ $purpurascens$ DSM2658 is isolated from protoplasts which are prepared in accordance with D. A. Hopwood et al. (1985) and frozen down at −20° C.

The protoplasts of strain $S.$ $purpurascens$ DSM2658 are thawed rapidly at 37° C. and then centrifuged in a bench centrifuge (Z 231M, from Hermle) at 3000 rpm for 7 minutes. The sedimented protoplasts are lysed at 60° C. for 1 hour in 10 mM Tris-HCl, 5 mM EDTA, pH 7.8, 0.5% SDS and 0.2 mg/ml proteinase K. The mixture is adjusted to 5 mM EDTA, pH 8.0, 1% SDS and 1M NaCl and placed in ice water for 2 hours. Following centrifugation at 10,000 rpm for 30 min at 4° C., the supernatant is transferred into a 1.5 ml Eppendorf tube, the lid of which has a hole pierced by a red-hot spatula. A dialysis membrane is stretched between the opening of the tube and its lid, and the lid is then closed and sealed with parafilm. The tube is then dialyzed twice at 4° C. for 5 hours in 0.5 liter 10 mM Tris-HCl, pH 7.5.

10 µg of total DNA isolated from each of the Streptomycetes strains investigated are incubated at 37° C. for 2 hours in 10 mM Tris/HCl, pH 8.0, 5 mM MgCl$_2$, 100mM NaCl and 1 mM mercaptoethanol together with 10 U BamHI and 1 U DNase-free bovine pancreatic RNase (Boehringer Mannheim, Germany).

The cleaved Streptomycetes genomic DNA and the molecular weight standards (HindIII and EcoRI/Hind-III fragments of λ DNA, Boehringer Mannheim) are fractionated on an 0.8% agarose gel and then photographed under UV illumination (254 nm).

4. Transfer of DNA to Membranes (Southern Transfer)

DNA fragments are transferred from agarose gels to membranes essentially in accordance with the method described by E. M. Southern (1975) J. Mol. Biol. 98: 503–517. The agarose gel obtained in accordance with point 3 is tilted in 0.24M hydrochloric acid for 15 minutes and then treated for 20 minutes with 0.4M sodium hydroxide solution. The gel is laid on 2 layers of absorbent paper (Whatman 3MM-Chr, from Whatman International Ltd., Maidstone, England), and a Hybond™-N+ membrane (from Amersham, Braunschweig, Germany) is stretched over it while ensuring that no air bubbles are trapped. As described in J. Sambrook et al. (1989), a plurality of layers of absorbent paper are then stacked on the membrane. A weight of approximately 1 kg is then placed on the filter paper stack. The DNA is transferred by 0.4M sodium hydroxide solution being sucked through. After transfer has taken place for 16 hours, the nylon filter is briefly rinsed with 0.9M sodium chloride and 0.09M trisodiumcitrate, and then baked at 80° C. for 2 hours in a drying oven.

5. DNA Hybridization and Autoradiography

The nylon filter, which is treated as described under point 4, is tilted at 68° C. for two hours in 50 ml of prehybridization solution (0.9M sodium chloride; 0.09M trisodium citrate, 0.5% SDS, 20 µg/ml denatured herring sperm DNA, 0.1% bovine serum albumin (fraction V, sigma), 0.1% ficoll (type 400, from Sigma, 0.1% polyvinylpyrrolidone MW=approximately 40,000 d, from Sigma). The prehybridization solution is poured off and 50 ml of hybridization solution, which contains the denatured strD or strE gene probe in prehybridization solution without herring sperm DNA, is added. The hybridization is carried out at 68° C. for 16 hours while shaking gently. The filters are then washed at 68° C. for 15 minutes in 0.3M sodium chloride, 0.03M trisodium citrate and 0.5% SDS, and then at 68° C. 3 times for 15 minutes in 0.075M sodium chloride, 0.0075M trisodium citrate and 0.5% SDS. The filters are dried at room temperature, laid on a Whatman 3MM-Chr filter paper and covered with vacuum-sealing foil. Autoradiography is carried out at −80° C. for at least 16 hours using Kodak X-Omat AR X-ray films in a light-proof cassette equipped with intensifying screens.

TABLE 1

Hybridization of BamHI fragments from the total DNA of different actinomycetes with $^{32}$P-labeled strD and strE gene probes.

| Total DNA from | Producer of | BamHI fragments (kb) hybridizing with gene probe | |
|---|---|---|---|
| | | strD | strE |
| S. nodosus DSM40109 | amphotericin A,B | 2.6 | 2.4 |
| | | | 4.4 |
| S. nodosus NRRLB-2371 | amphotericin A,B | 2.6 | 2.4 |
| | | | 4.4 |
| S. noursei DSM40635 | nystatin | 3.0 | 3.0 |
| | | | 2.2 |
| S. noursei NRRLB-1714 | nystatin | 3.0 | 3.0 |
| | | | 2.2 |
| S. aminophilus DSM40186 | perimycin | 7.0 | 7.0 |
| | | | 3.5 |
| S. lucensis DSM40317 | lucensomycin | 1.0 | 11.0 |
| S. venezuelae NRRLB-2447 | methymycin | | 9.0 |
| S. narbonensis DSM40016 | narbomycin | 5.0 | 5.0 |
| | | 4.0 | |
| S. purpurascens DSM2658 | rhodomycin | 5.7 | 5.7 |
| S. griseus DSM40236 | streptomycin | 9.0 | 9.0 |
| S. glaucescens DSM40716 | hydroxystrepto-mycin | 5.0 | 5.0 |

S. = Streptomyces

6. Isolation and Cloning of BamHI Fragments from the Total DNA of *Streptomyces nodosus* DSM40109

The total DNA from *S. nodosus* DSM40109 is isolated, cleaved completely with BamHI and fractionated by agarose gel electrophoresis (see Example 3). BamHI fragments which are from 1.5 to 3 kb in length are isolated out of the gel (see Example 1).

The vector plasmid is isolated from the strain *S. coelicolor* Müller DSM4914 pEB15 by the method described in D. A. Hopwood et al. (1985) p. 85 ff., and then cleaved with BglII and treated with alkaline phosphatase (calf intestinal phosphatase, Boehringer Mannheim, Germany) in accordance with the methods described in EP-0-368-224 (Example 2). In each case, 1 µg of the BglII-cleaved, dephosphorylated vector DNA is incubated at 16° C. for 16 hours in a 20 µl reaction mixture containing 5 µg of isolated 1.5 kb to 3 kb BamHI fragments from the total DNA of *S. nodosus* DSM40109 and 1 U of T4 DNA ligase (Boehringer Mannheim) in ligase buffer (66 mM Tris-HCl, pH 7.5, 5 mM MgCl$_2$, 1 mM dithiothreitol, 1 mM ATP). Protoplasts of *S. sp.* DSM40434 are prepared in accordance with D. A. Hopwood et al. pages 12 ff. The ligase mixture is transformed into *S. lividans* DSM40434 protoplasts as described in Hopwood et al. pages 110 ff. Thiostreptone-resistant transformants are cultivated at 30° C. for 3 days in 2.5 ml of CASO broth (Merck, Darmstadt) to which 30 µg/ml thiostreptone has been added. The plasmid DNA is isolated by the method described in Hopwood et al. pages 85 ff., cut with ClaI and fractionated by gel electrophoresis. At least 30% of the transformants investigated harbor a plasmid of the size of 6.8 kb to 8.3 kb.

7. Identification of Clones Which Contain dTDP-D-Glucose Synthase Genes

In each case, ten of the clones obtained in accordance with Example 6 are cultivated at 30° C. for three days in 2.5 ml of CASO broth containing 30 µg/ml thiostreptone. The plasmid DNA is then isolated from a total of 200 of these so-called pools of ten (Hopwood, pages 85 ff.). 5 µl of each of the isolated plasmid DNA samples is heated at 96° C. for 10 minutes and then cooled rapidly in ice water. 3 µl of the denatured plasmid DNA from each pool are then transferred onto a membrane (Hybond™-N+, Amersham Buchler, Braunschweig, Germany) in a regular pattern at intervals of 1.5 cm in each case. After having been dried at room temperature, the membrane is laid for 5 minutes on a filter paper (Whatman 3MM-Chr, Whatman International Ltd. Maidstone, England) which has been soaked in denaturation buffer I (1.5M NaCl, 0.5M NaOH). Subsequently, filter papers are employed for 1 min and 20 min which have been soaked in neutralization solution (1.5M NaCl, 0.5M Tris-HCl, pH 7.2, 1 mM EDTA) and denaturation buffer II (0.4M NaOH), respectively. The Hybond™-N+ membrane is rinsed with 5-fold concentrated SSC solution (corresponds to 0.75M sodium chloride, 0.075M trisodium citrate, pH 7.5), and then hybridized with the strD probe (see Example 2) as described in Example 5. 3 out of 200 pools of ten hybridize with this probe. A selected pool is split into the ten individual clones whose plasmid DNA is then isolated and hybridized with the strD probe (see Example 2) as described in Example 5. The hybridizing plasmid is designated pPS72.2 (see FIG. 3B). It contains a 2.6 kb BamHI fragment cloned into the vector pEB15.

8. Subcloning of Plasmid pPS72.2

Plasmid pPS72.2 is isolated by cesium chloride density gradient centrifugation from the *S. lividans* clone isolated in accordance with Examples 6 and 7 (Hopwood et al., pp. 87, 82 and 93). The plasmid is cleaved with SmaI and SstI, and the resultant 1.4 kb SmaI/SstI fragment is isolated out of the gel. The vector plasmid pUC18 is obtained from Boehringer Mannheim, Germany, and cut with SmaI and SstI, and the 2.7 kb fragment is isolated. 1 µg of each of the isolated 1.4 kb and 2.7 kb fragments are together treated with T4 DNA ligase and then transformed into competent *E. coli* DH5alpha cells (MAX Efficiency DH5Alpha™ competent cells, Gibco BRL, Eggenstein, Germany) in accordance with the manufacturer's instructions and selected at 37° C. for 16 hours on LB plates (see Example 1) containing 100 µg/ml ampicillin. Ampicillin-resistant colonies are cultured at 37° C. for 16 hours in 2.5 ml of LB medium containing 100 µg/ml ampicillin, and the plasmid DNA is isolated by alkaline minilysis (J. Sambrook et al. 1989, 1.25 to 1.28), digested with SmaI and SstI, and fractionated by gel electrophoresis. A plasmid which contains a 1.4 kb SmaI/SstI fragment is designated pPS1 (see FIG. 3B).

The plasmid pPS72.2 is cleaved with SmaI and the 1.45 kb SmaI fragment is isolated. SmaI-linearized, dephosphorylated vector pUC18 is obtained from Boehringer Mannheim, Germany. 1 µg each of the isolated 1.45 kb SmaI fragment from pPS72.2 and the SmaI-linearized, dephosphorylated vector pUC18 are joined by T4 DNA ligase and transformed into competent *E. coli* DH5alpha cells. Plasmid DNA is isolated from resultant ampicillin-resistant clones, cut with EcoRI and fractionated by gel electrophoresis. A plasmid possessing a 0.4 kb EcoRI fragment is designated pSab1 and contains the 1.45 kb SmaI fragment cloned in pUC18 in the orientation shown in FIG. 3B.

Plasmid pSab1 is digested with EcoRI. The resultant 3.7 kb fragment is isolated, religated with T4 DNA ligase, and transformed into *E. coli* DH5alpha. The 3.7 kb plasmid which is obtained is designated pSab3 (see FIG. 3B).

Plasmid pSab1 is cleaved with EcoRI, and the 0.4 kb EcoRI fragment is isolated, ligated with EcoRI-linearized, dephosphorylated vector pUC18, and transformed into competent E. coli DH5alpha cells. Ampicillin-resistant transformants containing plasmid DNA are isolated and cleaved with SmaI. A plasmid possessing a 0.4 kb SmaI fragment is designated pSab2.1 (see FIG. 3B). A plasmid containing a 3.1 kb SmaI fragment is designated pSab2.2 (see FIG. 3B).

9. Analysis of the DNA Sequence of the 2.6 kb BamHI Fragment From S. nodosus DSM40109

Following alkaline lysis, the plasmids pPS72.2, pPS1, pSab1, pSab2.1, pSab2.2 and pSab3 (see FIGS. 3A and B) are purified by being subjected twice to cesium chloride density gradient centrifugation (see J. Sambrook et al., 1989, 1.38 to 1.43).

Two primers (pUC, sequencing and reverse-sequencing) are obtained from Boehringer, Mannheim, Germany. The other primers listed in Table 2 are synthesized as described in EP-A-0-368-224, Example 16. The sequences of the primers which were used for sequencing plasmids pPS72.2, pPS1, pSab1, pSab2.1, pSab2.2 and pSab3 are collated in Table 2.

The double-stranded DNA of the 2.6 kb BamHI fragment from S. nodosus DSM40109 was sequenced with the Promega fmol™ sequencing system (Serva, Heidelberg, Germany) using 6 μCi [$^{35}$S]-deoxyadenosine-5'- [alphathio]-triphosphate (1422 μCi/mmol), DuPont de Nemours, NEN Division, Dreieich, Germany.

The so-called annealing temperature ($T_A$), at which the respective primer binds to the template DNA, is listed in Table 2. Denaturation, primer-binding (annealing) and TaqI polymerase reaction (elongation) are carried out in a Perkin Elmer Cetus DNA Thermal Cycler, Bodenseewerk, Überlingen, Germany. In this procedure, after heating at 95° C. for 2 min, the temperature programs 1 (30 sec 95° C., 30 sec $T_A$, 1 min 70° C.) or 2 (30 sec 95° C., 30 sec. $T_A$, 70° C.) will pass through in 30 cycles in each case, as indicated in Table 2.

TABLE 2

The primers used for sequencing the DNA of the 2634-bp BamHI fragment from the total DNA of Streptomyces nodosus DSM40109

| Primer[1]) | Primer Sequence | $T_A$ in °C. | T profile |
|---|---|---|---|
| $P_{seq}$[2]) | 5'-d[GTAAAACGACGGCCAGT]-3'SEQ ID NO:1 | 47 | 1 |
| $P_{revseq}$[2]) | 5'-d[CAGGAAACAGCTATGAC]-3' SEQ ID NO:2 | 45 | 1 |
| $P_{1mel}$[3]) | 5'-d[GGCACCACACCCCCGAG]-3' SEQ ID NO:3 | 55 | 2 |
| $P_{2mel}$[3]) | 5'-d[GTGACCGTCCGGCCCTG]-3' SEQ ID NO:4 | 55 | 2 |
| $P_{91}$ | 5'-d[ATCCGCAGGTCCACCACGA]-3' SEQ ID NO:5 | 57 | 2 |
| $P_{144}$ | 5'-d[GGCAGGTCCGTCTACGT]-3'SEQ ID NO:6 | 51 | 1 |
| $P_{rev160}$ | 5'-d[ACGTAGACGGACCTGCC]-3' SEQ ID NO:7 | 51 | 1 |
| $P_{321}$ | 5'-d[GACAAGGACGCGAAGGC]-3'SEQ ID NO:8 | 51 | 1 |
| $P_{rev337}$ | 5'-d[GCCTTCGCGTCCTTGTC]-3'SEQ ID NO:9 | 51 | 1 |
| $P_{rev567}$ | 5'-d[AGATCGGTGGTCGCGAT]-3'SEQ ID NO:10 | 54 | 1 |
| $P_{603}$ | 5'-d[GCAACCCCGAGGAGATC]-3'SEQ ID NO:11 | 51 | 1 |
| $P_{691}$ | 5'-d[TCGGATGCTTGAGTTCT]-3'SEQ ID NO:12 | 45 | 1 |
| $P_{rev711}$ | 5'-d[CGGCAGAACTCAAGCAT]-3'SEQ ID NO:13 | 47 | 1 |
| $P_{903}$ | 5'-d[ATGTGTTCGTGGACATC]-3'SEQ ID NO:14 | 45 | 1 |
| $P_{rev919}$ | 5'-d[GATGTCCACGAACACAT]-3'SEQ ID NO:15 | 45 | 1 |
| $P_{1284}$ | 5'-d[GGCTGAACGCCGGTGTG]-3'SEQ ID NO:16 | 53 | 1 |
| $P_{rev1300}$ | 5'-d[CACACCGGCGTTCAGCC]-3'SEQ ID NO:17 | 53 | 1 |
| $P_{1633}$ | 5'-d[CTGATCCCCATCGCCAA]-3'SEQ ID NO:18 | 49 | 1 |
| $P_{rev1649}$ | 5'-d[TTGGCGATGGGGATCAG]-3'SEQ ID NO:19 | 49 | 1 |
| $P_{1853}$ | 5'-d[ACGACGACTTCGTGATG]-3'SEQ ID NO:20 | 47 | 1 |
| $P_{rev1869}$ | 5'-d[CATCAGGAAGTCGTCGT]-3'SEQ ID NO:21 | 47 | 1 |
| $P_{rev1997}$ | 5'-d[AGTTCGGCGACGCCGAA]-3'SEQ ID NO:22 | 51 | 1 |
| $P_{rev2033}$ | 5'-d[TTCTACACCAGGCGCAGCACCTCC]-3'SEQ ID NO:23 | 70 | 2 |
| $P_{2071}$ | 5'-d[GTCTACTTCTTCACCGCCGCCATC]-3'SEQ ID NO:24 | 70 | 2 |
| $P_{2156}$ | 5'-d[TCCAGTGGTTGGTCACC]-3'SEQ ID NO:25 | 49 | 1 |
| $P_{2231}$ | 5'-d[TCGAGGACGTCCTTGAGTGCAACA]-3'SEQ ID NO:26 | 70 | 2 |
| $P_{rev2258}$ | 5'-d[GGCTGTTGCACTCAAGG]-3'SEQ ID NO:27 | 49 | 1 |
| $P_{2306}$ | 5'-d[ACAGCGTGCTCGTCGGC]-3'SEQ ID NO:28 | 53 | 1 |
| $P_{2473}$ | 5'-d[GGCTCCATCGCCCTGGA]-3'SEQ ID NO:29 | 53 | 1 |
| $P_{rev2489}$ | 5'-d[TCCAGGGCGATGGAGCC]-3'SEQ ID NO:30 | 53 | 1 |

[1])The primers are designated in accordance with their binding site (first nucleotide position) on the BamHI fragment.
[2])The primers are obtained from Boehringer Mannheim, Germany.
[3])The expression [mel'] designates hybridization of the primer with the melanine biosynthesis gene cluster which occurs in some vectors which are used for the DNA sequencing.

After adding stop solution (see fmol™ DNA sequencing system), the four sample mixtures are fractionated on a 6% polyacrylamide-urea gel. For this, the Macrophor sequencing chamber, Pharmacia Biosystems GmbH, Freiburg, Germany, is used. The glass plates are precleaned with absolute ethanol. The glass plate with the cut out is rubbed down with 8 ml of absolute alcohol to which is added 240 μl of 10% acetic acid and 40 μl of binding silane (Pharmacia). The thermoplate is treated with 5 ml of repellent silane (Pharmacia). Subsequently, each is then polished with absolute ethanol.

The 6% polyacrylamide-urea gel comprises 6% acrylamide/bisacrylamide (19:1), 7M urea in TBE [0.1M Tris, 89 mM boric acid, 1 mM EDTA (ethylenediaminetetraacetate)]. 0.06% ammonium persulfate and 0.1% TEMED (N,N,N', N'-tetramethylethylenediamine) are added for the polymerization. Before pouring, the solution is filtered through a cellulose nitrate membrane (Nalgene® type S, pore diameter 0.2 μm, Oskar Glock, Offenbach) and degassed.

The fractionation is carried out in TBE buffer at 60° C. for 1.5 h or 3.5 h and at 2400 V. The gel is subsequently tilted for 10 min in 10% acetic acid, and then briefly rinsed with water and dried at 65° C. for 30 min. Autoradiography is carried out at room temperature for 1 to 3 days using Kodak X-OmaT™ XAR5 films in an exposure cassette equipped with intensifying screens (Dr Goos Suprema Universal). The X-ray film is developed in a developing machine (Agfa Gevaert).

The DNA sequence of the 2634-kb BamHI fragment is depicted in FIG. 4. The DNA sequence (SEQ ID NO:31) which was obtained is translated into the corresponding amino acid sequence (SEQ ID NOS:32, 33 and 34) from nucleotide positions Nos. 1 to 401. The codon usage in this segment (snoM gene segment) corresponds to the codon usage which is characteristic for Streptomycetes genes (F. Wright et al., 1992, gene 113:55–65). A stop codon (TGA) is present at nucleotide position No. 402. The identified open reading frame encompasses 133 amino acid residues. Comparison of this amino acid sequence with the EMBL database (TFASTA program of the database searching program of the GCG package, version 7, Genetics Computer Group Inc. Madison, Wis., U.S.A.) indicates 42% agreement with the C terminal part (amino acid positions Nos. 59 to 201) of the dTDP-4-keto-6-deoxy-D-glucose 3,5-epimerase (strM) of *S. griseus* DSM40236. On the basis of comparison of the biosynthesis pathways of dTDP-L-dihydrostreptose (FIG. 1) and dTDP-D-mycosamine (FIGS. 3A, 3B and 4), the snoM gene product is therefore designated dTDP-4-keto-6-deoxy-D-glucose 3,4-isomerase.

An additional open reading frame (snoT gene segment) is located from nucleotide positions Nos. 416 to 1532. The deduced amino acid sequence encompasses 372 residues. In the region of amino acid positions Nos. 259 to 340, there is 29% agreement with the corresponding part (amino acid positions Nos. 329 to 412) of the flavonol-O-3-glucosyl transferase of corn. For this reason, the snoT gene product is designated amphotheronolide B-dTDP-mycosaminyl transferase.

An additional open reading frame (snoD gene segment) is located from nucleotide positions Nos. 1561 to 2625. The corresponding gene product (355 amino acid residues) possesses 54% sequence identity with the dTDP-D-glucose synthase from *S. griseus* DSM40236, and is therefore designated dTDP-D-glucose synthase (see FIG. 1 and FIGS. 3A, 3B and 4).

We claim:

1. The DNA sequence of SEQ ID NO:31.

2. The DNA sequence as claimed in claim 1, which contains the complete snoT DNA sequence, encoding amphotheronolide B-dTDP-D-mycosaminyl transferase, the complete snoD DNA sequence, encoding dTDP-D-glucose synthase, and part of the DNA sequence of snoM, encoding dTDP-4-keto-6-deoxy-D-glucose isomerase.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

GTAAAACGAC GGCCAGT   17

( 2 ) INFORMATION FOR SEQ ID NO:2:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

CAGGAAACAG CTATGAC   17

( 2 ) INFORMATION FOR SEQ ID NO:3:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

GGCACCACAC CCCCGAG                                                                                          17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTGACCGTCC GGCCCTG                                                                                          17

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATCCGCAGGT CCACCACGA                                                                                        19

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGCAGGTCCG TCTACGT                                                                                          17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ACGTAGACGG ACCTGCC                                                                                          17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GACAAGGACG CGAAGGC                                                                                          17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCCTTCGCGT CCTTGTC      17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGATCGGTGG TCGCGAT      17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCAACCCCGA GGAGATC      17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TCGGATGCTT GAGTTCT      17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGGCAGAACT CAAGCAT      17

(2) INFORMATION FOR SEQ ID NO:14:

(i) SEQUENCE CHARACTERISTICS:
        (A) LENGTH: 17 base pairs
        (B) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

ATGTGTTCGT GGACATC 17

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

GATGTCCACG AACACAT 17

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GGCTGAACGC CGGTGTG 17

( 2 ) INFORMATION FOR SEQ ID NO:17:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CACACCGGCG TTCAGCC 17

( 2 ) INFORMATION FOR SEQ ID NO:18:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CTGATCCCCA TCGCCAA 17

( 2 ) INFORMATION FOR SEQ ID NO:19:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

TTGGCGATGG GGATCAG 17

( 2 ) INFORMATION FOR SEQ ID NO:20:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:20:

ACGACGACTT CGTGATG 17

( 2 ) INFORMATION FOR SEQ ID NO:21:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:21:

CATCAGGAAG TCGTCGT 17

( 2 ) INFORMATION FOR SEQ ID NO:22:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:22:

AGTTCGGCGA CGCCGAA 17

( 2 ) INFORMATION FOR SEQ ID NO:23:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:23:

TTCTACACCA GGCGCAGCAC CTCC 24

( 2 ) INFORMATION FOR SEQ ID NO:24:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:24:

GTCTACTTCT TCACCGCCGC CATC 24

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TCCAGTGGTT GGTCACC 17

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TCGAGGACGT CCTTGAGTGC AACA 24

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GGCTGTTGCA CTCAAGG 17

( 2 ) INFORMATION FOR SEQ ID NO:28:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

ACAGCGTGCT CGTCGGC 17

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GGCTCCATCG CCCTGGA 17

( 2 ) INFORMATION FOR SEQ ID NO:30:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:30:

TCCAGGGCGA TGGAGCC                                                                              17

( 2 ) INFORMATION FOR SEQ ID NO:31:

( i ) SEQUENCE CHARACTERISTICS:
( A ) LENGTH: 2634 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 3..401

( i x ) FEATURE:
( A ) NAME/KEY: CDS
( B ) LOCATION: 416..1531

( i x ) FEATURE:
( A ) NAME/KEY: CDS
( B ) LOCATION: 1561..2625

( x i ) SEQUENCE DESCRIPTION: SEQ ID NO:31:

| | | | | | | | | | | | | | | | |
|---|---|---|---|---|---|---|---|---|---|---|---|---|---|---|---|
| GG | ATC | CAC | AGT | GTG | CGC | ATA | CCG | CCC | GGG | CAG | GCC | AAG | TAC | GTC | ACC | 47 |
| | Ile | His | Ser | Val | Arg | Ile | Pro | Pro | Gly | Gln | Ala | Lys | Tyr | Val | Thr |
| | 1 | | | 5 | | | | | 10 | | | | | | 15 |
| TGC | GTC | CGC | GGG | GCG | CTG | CGC | GAC | CTC | GTG | GTG | GAC | CTG | CGG | ATC | GGC | 95 |
| Cys | Val | Arg | Gly | Ala | Leu | Arg | Asp | Leu | Val | Val | Asp | Leu | Arg | Ile | Gly |
| | | | | 20 | | | | | 25 | | | | | 30 | |
| TCC | CCG | ACC | TTC | GGC | GAG | CAC | CAG | GTC | AGC | GAA | CTG | GAC | GCG | AGC | TCC | 143 |
| Ser | Pro | Thr | Phe | Gly | Glu | His | Gln | Val | Ser | Glu | Leu | Asp | Ala | Ser | Ser |
| | | | 35 | | | | 40 | | | | | 45 | | | |
| GGC | AGG | TCC | GTC | TAC | GTC | CCC | GAG | GGC | GTG | GGC | CAC | GGA | TTC | CTG | GCG | 191 |
| Gly | Arg | Ser | Val | Tyr | Val | Pro | Glu | Gly | Val | Gly | His | Gly | Phe | Leu | Ala |
| | | 50 | | | | | 55 | | | | | 60 | | | |
| CTC | ACC | GAC | GAC | GCC | TGC | ATC | TGC | TAC | GTC | GTC | TCC | ACC | GCG | TAC | GTG | 239 |
| Leu | Thr | Asp | Asp | Ala | Cys | Ile | Cys | Tyr | Val | Val | Ser | Thr | Ala | Tyr | Val |
| | 65 | | | | | 70 | | | | | 75 | | | | |
| CCG | GGC | ACC | CAG | ATC | GAC | ATC | AAC | CCG | CTC | GAT | CCG | GAT | CTC | GCG | CTG | 287 |
| Pro | Gly | Thr | Gln | Ile | Asp | Ile | Asn | Pro | Leu | Asp | Pro | Asp | Leu | Ala | Leu |
| 80 | | | | | 85 | | | | | 90 | | | | | 95 |
| CCC | TGG | AAC | TGC | CCG | GAG | ACG | CCC | CTC | ATC | TCG | GAC | AAG | GAC | GCG | AAG | 335 |
| Pro | Trp | Asn | Cys | Pro | Glu | Thr | Pro | Leu | Ile | Ser | Asp | Lys | Asp | Ala | Lys |
| | | | | 100 | | | | | 105 | | | | | 110 | |
| GCG | CCG | ACC | GTG | GCC | GAG | GCC | GTA | CGG | GCA | GAC | CTC | CTG | CCC | CGA | TTC | 383 |
| Ala | Pro | Thr | Val | Ala | Glu | Ala | Val | Arg | Ala | Asp | Leu | Leu | Pro | Arg | Phe |
| | | | 115 | | | | | 120 | | | | | 125 | | |
| AGC | AAG | GCG | GGA | ACA | CCG | TGAGAATGCT | | CTTC | GTG | GCG | GCG | GGC | AGC | CCG | | 433 |
| Ser | Lys | Ala | Gly | Thr | Pro | | | | Met | Ala | Ala | Gly | Ser | Pro | |
| | | 130 | | | | | | | 1 | | | | | 5 | |
| GCG | ACG | GTG | TTC | GCC | CTG | GCC | CCG | CTG | GCC | ACC | GCC | GCC | CGC | AAC | GCG | 481 |
| Ala | Thr | Val | Phe | Ala | Leu | Ala | Pro | Leu | Ala | Thr | Ala | Ala | Arg | Asn | Ala |
| | | | 10 | | | | | 15 | | | | | 20 | | |
| GGT | CAC | CAG | GTC | GTC | ATG | GCC | GCG | AAC | GAC | GAC | ATG | GTT | CCG | GTC | ATC | 529 |
| Gly | His | Gln | Val | Val | Met | Ala | Ala | Asn | Asp | Asp | Met | Val | Pro | Val | Ile |
| | | 25 | | | | | 30 | | | | | 35 | | | |
| ACC | GCC | TCG | GGC | CTG | CCG | GGC | ATC | GCG | ACC | ACC | GAT | CTG | CCG | ATC | CGG | 577 |
| Thr | Ala | Ser | Gly | Leu | Pro | Gly | Ile | Ala | Thr | Thr | Asp | Leu | Pro | Ile | Arg |

|  |  |  |  |  |  |  |  |  |  |  |  |  |  |  |  |  |
|---|---|---|---|---|---|---|---|---|---|---|---|---|---|---|---|---|
|  |  |  | 40 |  |  |  | 45 |  |  |  |  | 50 |  |  |  |  |
| CAC | TTC | ATC | ACC | ACG | GAC | CGG | GCC | GGC | AAC | CCC | GAG | GAG | ATC | CCC | TCC | 625 |
| His | Phe | Ile | Thr | Thr | Asp | Arg | Ala | Gly | Asn | Pro | Glu | Glu | Ile | Pro | Ser |  |
| 55 |  |  |  |  | 60 |  |  |  |  | 65 |  |  |  |  | 70 |  |
| GAT | CCG | GTC | GAG | CAG | GCG | CTC | TTC | ACC | GGG | CGC | TGG | TTC | GCG | CGC | ATG | 673 |
| Asp | Pro | Val | Glu | Gln | Ala | Leu | Phe | Thr | Gly | Arg | Trp | Phe | Ala | Arg | Met |  |
|  |  |  |  | 75 |  |  |  |  | 80 |  |  |  |  | 85 |  |  |
| GCC | GCC | TCC | AGC | CTG | CCG | CGG | ATG | CTT | GAG | TTC | TGC | CGC | GCC | TGG | CGG | 721 |
| Ala | Ala | Ser | Ser | Leu | Pro | Arg | Met | Leu | Glu | Phe | Cys | Arg | Ala | Trp | Arg |  |
|  |  |  | 90 |  |  |  |  | 95 |  |  |  |  | 100 |  |  |  |
| CCC | GAC | CTG | ATC | GTC | GGC | GGC | ACG | ATG | AGC | TAC | GTC | GCC | CCG | CTG | CTG | 769 |
| Pro | Asp | Leu | Ile | Val | Gly | Gly | Thr | Met | Ser | Tyr | Val | Ala | Pro | Leu | Leu |  |
|  |  | 105 |  |  |  |  | 110 |  |  |  |  | 115 |  |  |  |  |
| GCC | CTG | CAC | CTC | GGC | GTG | CCG | CAT | GTG | CGC | CAG | ACC | TGG | GAC | GCC | ATC | 817 |
| Ala | Leu | His | Leu | Gly | Val | Pro | His | Val | Arg | Gln | Thr | Trp | Asp | Ala | Ile |  |
| 120 |  |  |  |  | 125 |  |  |  |  | 130 |  |  |  |  |  |  |
| GAG | GCC | GAC | GGC | ATC | CAT | CCC | GGC | GCG | GAC | GCC | GAA | CTC | CGT | CCG | GAA | 865 |
| Glu | Ala | Asp | Gly | Ile | His | Pro | Gly | Ala | Asp | Ala | Glu | Leu | Arg | Pro | Glu |  |
| 135 |  |  |  |  | 140 |  |  |  |  | 145 |  |  |  |  | 150 |  |
| CTC | GCG | GAG | TTC | GAC | CTC | GAC | CGG | CTG | CCC | TTA | CCC | GAT | GTG | TTC | GTG | 913 |
| Leu | Ala | Glu | Phe | Asp | Leu | Asp | Arg | Leu | Pro | Leu | Pro | Asp | Val | Phe | Val |  |
|  |  |  |  | 155 |  |  |  |  | 160 |  |  |  |  | 165 |  |  |
| GAC | ATC | TGC | CCG | CCG | AGC | CTG | CGG | CCG | GCC | GGC | GCC | GCC | CCG | GCC | CAG | 961 |
| Asp | Ile | Cys | Pro | Pro | Ser | Leu | Arg | Pro | Ala | Gly | Ala | Ala | Pro | Ala | Gln |  |
|  |  |  | 170 |  |  |  |  | 175 |  |  |  |  | 180 |  |  |  |
| CCG | ATG | CGG | TAC | GTC | CCG | GCC | AAC | GCC | CAG | CGG | CGG | CTG | GAG | CCC | TGG | 1009 |
| Pro | Met | Arg | Tyr | Val | Pro | Ala | Asn | Ala | Gln | Arg | Arg | Leu | Glu | Pro | Trp |  |
|  |  | 185 |  |  |  |  | 190 |  |  |  |  | 195 |  |  |  |  |
| ATG | TAC | CGC | CGG | GGC | GAG | CGC | CGC | CGC | GTC | CTG | GTG | ACG | TCC | GGG | AGC | 1057 |
| Met | Tyr | Arg | Arg | Gly | Glu | Arg | Arg | Arg | Val | Leu | Val | Thr | Ser | Gly | Ser |  |
| 200 |  |  |  |  | 205 |  |  |  |  | 210 |  |  |  |  |  |  |
| CGG | GTC | GCC | AAG | GAG | AGC | TAC | GAC | AAG | AAC | TTC | GAA | TTC | CTG | CGC | GGC | 1105 |
| Arg | Val | Ala | Lys | Glu | Ser | Tyr | Asp | Lys | Asn | Phe | Glu | Phe | Leu | Arg | Gly |  |
| 215 |  |  |  |  | 220 |  |  |  |  | 225 |  |  |  |  | 230 |  |
| CTC | GCC | AAG | GAC | GTC | GCC | GCC | TGG | GAC | GTC | GAG | CTG | ATC | GTC | GCC | GCG | 1153 |
| Leu | Ala | Lys | Asp | Val | Ala | Ala | Trp | Asp | Val | Glu | Leu | Ile | Val | Ala | Ala |  |
|  |  |  |  | 235 |  |  |  |  | 240 |  |  |  |  | 245 |  |  |
| CCG | GAA | GCG | GTC | GCC | GAC | GCC | CTG | CAC | GAC | GAA | CTG | CCG | GGC | ATC | CGG | 1201 |
| Pro | Glu | Ala | Val | Ala | Asp | Ala | Leu | His | Asp | Glu | Leu | Pro | Gly | Ile | Arg |  |
|  |  |  | 250 |  |  |  |  | 255 |  |  |  |  | 260 |  |  |  |
| GCC | GGC | TGG | GCA | CCG | CTC | GAC | GTG | GTG | GCG | CCC | ACC | TGC | GAT | GTG | CTC | 1249 |
| Ala | Gly | Trp | Ala | Pro | Leu | Asp | Val | Val | Ala | Pro | Thr | Cys | Asp | Val | Leu |  |
|  |  | 265 |  |  |  |  | 270 |  |  |  |  | 275 |  |  |  |  |
| GTG | CAC | CAC | GGG | GGC | GGC | GTC | AGC | ACC | CTG | ACC | GGG | CTG | AAC | GCC | GGT | 1297 |
| Val | His | His | Gly | Gly | Gly | Val | Ser | Thr | Leu | Thr | Gly | Leu | Asn | Ala | Gly |  |
| 280 |  |  |  |  | 285 |  |  |  |  | 290 |  |  |  |  |  |  |
| GTG | CCC | CAA | CTG | CTC | ATT | CCG | CGG | GGC | GCC | GTG | CTG | GAG | AAG | CCG | GCC | 1345 |
| Val | Pro | Gln | Leu | Leu | Ile | Pro | Arg | Gly | Ala | Val | Leu | Glu | Lys | Pro | Ala |  |
| 295 |  |  |  |  | 300 |  |  |  |  | 305 |  |  |  |  | 310 |  |
| CTT | CGC | GTC | GCC | GAT | CAC | GGG | GCA | GCG | ATC | ACG | CTG | CTG | CCC | GGC | GAG | 1393 |
| Leu | Arg | Val | Ala | Asp | His | Gly | Ala | Ala | Ile | Thr | Leu | Leu | Pro | Gly | Glu |  |
|  |  |  |  | 315 |  |  |  |  | 320 |  |  |  |  | 325 |  |  |
| GAC | GCG | GCC | GAC | GCG | ATC | GCA | GAC | TCC | TGT | CAG | GAA | CTG | CTG | TCC | AAG | 1441 |
| Asp | Ala | Ala | Asp | Ala | Ile | Ala | Asp | Ser | Cys | Gln | Glu | Leu | Leu | Ser | Lys |  |
|  |  |  | 330 |  |  |  |  | 335 |  |  |  |  | 340 |  |  |  |
| GAC | ACC | TAC | GGC | GAG | CGG | GCC | CGC | GAA | CTC | TCC | CGG | GAG | ATC | GCC | GCC | 1489 |
| Asp | Thr | Tyr | Gly | Glu | Arg | Ala | Arg | Glu | Leu | Ser | Arg | Glu | Ile | Ala | Ala |  |
|  |  | 345 |  |  |  |  | 350 |  |  |  |  | 355 |  |  |  |  |
| ATG | CCC | TCG | CCC | GCG | AGC | GTG | GTC | GAC | GCG | CTC | GAA | CCG | GCA |  |  | 1531 |
| Met | Pro | Ser | Pro | Ala | Ser | Val | Val | Asp | Ala | Leu | Glu | Pro | Ala |  |  |  |

|  |  |  |  |  |  |  |  |  |
|---|---|---|---|---|---|---|---|---|
| | 360 | | | 365 | | | 370 | |

```
TGAATACACG AAACCGAGAG GACCTCTCG ATG AAG GCT CTG GTG CTC GCC GGC                1584
                                   Met Lys Ala Leu Val Leu Ala Gly
                                    1               5

GGA TCT GGT ACC CGC CTG CGG CCT TTC AGT TAT TCG ATG CCC AAA CAA                1632
Gly Ser Gly Thr Arg Leu Arg Pro Phe Ser Tyr Ser Met Pro Lys Gln
         10              15              20

CTG ATC CCC ATC GCC AAC ACA CCC GTG CTG GTG CAT GTG CTG AAC GCC                1680
Leu Ile Pro Ile Ala Asn Thr Pro Val Leu Val His Val Leu Asn Ala
25              30              35                              40

GTC CGG GAG CTG GGC GTG ACC GAG GTC GGC GTC ATC GTC GGC AAC CGC                1728
Val Arg Glu Leu Gly Val Thr Glu Val Gly Val Ile Val Gly Asn Arg
                 45              50              55

GGC CCC GAG ATC GAG GCC GTG CTC GGC GAC GGT GCC CGG TTC GAC GTG                1776
Gly Pro Glu Ile Glu Ala Val Leu Gly Asp Gly Ala Arg Phe Asp Val
             60              65              70

CGC ATC ACC TAC ATC CCC CAG GAC GCA CCG CGC GGA CTG GCC CAC ACC                1824
Arg Ile Thr Tyr Ile Pro Gln Asp Ala Pro Arg Gly Leu Ala His Thr
                 75              80              85

GTG TCC ATC GCC CGC GGC TTC CTC GGC GAC GAC GAC TTC GTG ATG TAC                1872
Val Ser Ile Ala Arg Gly Phe Leu Gly Asp Asp Asp Phe Val Met Tyr
         90              95              100

CTC GGC GAC AAC ATG CTG CCC GAC GGA GTC ACC GAG ATC GCC GAG GAG                1920
Leu Gly Asp Asn Met Leu Pro Asp Gly Val Thr Glu Ile Ala Glu Glu
105             110             115                             120

TTC ACC CGG CAG CGC CCG GCC GCC CAG GTC GTC GTG CAC AAG GTC CCC                1968
Phe Thr Arg Gln Arg Pro Ala Ala Gln Val Val Val His Lys Val Pro
                125             130             135

GAC CCG CGC TCC TTC GGC GTC GCC GAA CTC GGC CCC GAC GGG GAG GTG                2016
Asp Pro Arg Ser Phe Gly Val Ala Glu Leu Gly Pro Asp Gly Glu Val
            140             145             150

CTG CGC CTG GTG GAG AAG CCG TGG CAG CCG CGC AGC GAC ATG GCC CTG                2064
Leu Arg Leu Val Glu Lys Pro Trp Gln Pro Arg Ser Asp Met Ala Leu
        155             160             165

ATC GGG GTC TAC TTC TTC ACC GCC GCC ATC CAC CAG GCG GTG GCG GCC                2112
Ile Gly Val Tyr Phe Phe Thr Ala Ala Ile His Gln Ala Val Ala Ala
170             175             180

ATC TCG CCC AGC AGC CGC GGC GAA CTG GAG ATC ACC GAC GCC GTC CAG                2160
Ile Ser Pro Ser Ser Arg Gly Glu Leu Glu Ile Thr Asp Ala Val Gln
185             190             195                             200

TGG TTG GTC ACC TCC GGC GCG GAC GTG CGC GCC AGC CTC TAC GAC GGC                2208
Trp Leu Val Thr Ser Gly Ala Asp Val Arg Ala Ser Leu Tyr Asp Gly
                205             210             215

TAC TGG AAG GAC ACC GGG AGG GTC GAG GAC GTC CTT GAG TGC AAC AGC                2256
Tyr Trp Lys Asp Thr Gly Arg Val Glu Asp Val Leu Glu Cys Asn Ser
            220             225             230

CAC CTC CTG GAC GGC CTG ACC CCG CGC GTC GAC GGA CAG GTC GAC GCC                2304
His Leu Leu Asp Gly Leu Thr Pro Arg Val Asp Gly Gln Val Asp Ala
        235             240             245

GAC AGC GTG CTC GTC GGC CGG GTC GTG ATC GAG GCG GGG GCG CGC ATC                2352
Asp Ser Val Leu Val Gly Arg Val Val Ile Glu Ala Gly Ala Arg Ile
250             255             260

GTG CGG TCG CGG GTC GAG GGC CCG GCG ATC ATC GGC GCG GGC ACG GTC                2400
Val Arg Ser Arg Val Glu Gly Pro Ala Ile Ile Gly Ala Gly Thr Val
265             270             275                             280

CTT CAG GAC AGC CAG GTG GGC CCG CAC ACC TCC ATC GGG CGG GAC TGC                2448
Leu Gln Asp Ser Gln Val Gly Pro His Thr Ser Ile Gly Arg Asp Cys
                285             290             295

ACG GTG ACG GAC AGC CGG CTG GAG GGC TCC ATC GCC CTG GAC GAG GCG                2496
Thr Val Thr Asp Ser Arg Leu Glu Gly Ser Ile Ala Leu Asp Glu Ala
```

|     |     |     |     |     |     |     |     |     |     |     |     |     |     |     |     |
|---|---|---|---|---|---|---|---|---|---|---|---|---|---|---|---|
| | | 300 | | | | 305 | | | | | 310 | | | | |

```
TCG  GTC  ACC  GGC  GTG  CGC  GGC  CTG  CGC  AAC  TCG  CTG  ATC  GGG  CGC  GCC       2544
Ser  Val  Thr  Gly  Val  Arg  Gly  Leu  Arg  Asn  Ser  Leu  Ile  Gly  Arg  Ala
          315            320                      325

GCG  TCC  GTC  GGC  ACC  ACC  GGC  CCC  GGC  ACG  GGC  CAT  CAC  TGC  CTG  GTC       2592
Ala  Ser  Val  Gly  Thr  Thr  Gly  Pro  Gly  Thr  Gly  His  His  Cys  Leu  Val
     330                 335                      340

GTC  GGA  GAC  CAC  ACC  CGA  GTG  GAG  GTC  GCG  GCA  TGAGGATCC                      2634
Val  Gly  Asp  His  Thr  Arg  Val  Glu  Val  Ala  Ala
345                 350                 355
```

( 2 ) INFORMATION FOR SEQ ID NO:32:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Ile  His  Ser  Val  Arg  Ile  Pro  Pro  Gly  Gln  Ala  Lys  Tyr  Val  Thr  Cys
1                  5                   10                      15

Val  Arg  Gly  Ala  Leu  Arg  Asp  Leu  Val  Val  Asp  Leu  Arg  Ile  Gly  Ser
               20                  25                       30

Pro  Thr  Phe  Gly  Glu  His  Gln  Val  Ser  Glu  Leu  Asp  Ala  Ser  Ser  Gly
          35                      40                       45

Arg  Ser  Val  Tyr  Val  Pro  Glu  Gly  Val  Gly  His  Gly  Phe  Leu  Ala  Leu
     50                       55                      60

Thr  Asp  Asp  Ala  Cys  Ile  Cys  Tyr  Val  Val  Ser  Thr  Ala  Tyr  Val  Pro
65                  70                       75                           80

Gly  Thr  Gln  Ile  Asp  Ile  Asn  Pro  Leu  Asp  Pro  Asp  Leu  Ala  Leu  Pro
                    85                       90                      95

Trp  Asn  Cys  Pro  Glu  Thr  Pro  Leu  Ile  Ser  Asp  Lys  Asp  Ala  Lys  Ala
               100                      105                 110

Pro  Thr  Val  Ala  Glu  Ala  Val  Arg  Ala  Asp  Leu  Leu  Pro  Arg  Phe  Ser
          115                      120                 125

Lys  Ala  Gly  Thr  Pro
          130
```

( 2 ) INFORMATION FOR SEQ ID NO:33:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Val  Ala  Ala  Gly  Ser  Pro  Ala  Thr  Val  Phe  Ala  Leu  Ala  Pro  Leu  Ala
1                   5                   10                      15

Thr  Ala  Ala  Arg  Asn  Ala  Gly  His  Gln  Val  Val  Met  Ala  Ala  Asn  Asp
               20                  25                       30

Asp  Met  Val  Pro  Val  Ile  Thr  Ala  Ser  Gly  Leu  Pro  Gly  Ile  Ala  Thr
          35                      40                       45

Thr  Asp  Leu  Pro  Ile  Arg  His  Phe  Ile  Thr  Thr  Asp  Arg  Ala  Gly  Asn
     50                       55                      60

Pro  Glu  Glu  Ile  Pro  Ser  Asp  Pro  Val  Glu  Gln  Ala  Leu  Phe  Thr  Gly
65                  70                       75                           80
```

| | | | | | | | | | | | | | | |
|---|---|---|---|---|---|---|---|---|---|---|---|---|---|---|
|Arg|Trp|Phe|Ala|Arg<br>85|Met|Ala|Ala|Ser|Ser<br>90|Leu|Pro|Arg|Met|Leu<br>95|Glu|
|Phe|Cys|Arg|Ala<br>100|Trp|Arg|Pro|Asp|Leu<br>105|Ile|Val|Gly|Gly|Thr<br>110|Met|Ser|
|Tyr|Val|Ala<br>115|Pro|Leu|Leu|Ala|Leu<br>120|His|Leu|Gly|Val|Pro<br>125|His|Val|Arg|
|Gln|Thr<br>130|Trp|Asp|Ala|Ile|Glu<br>135|Ala|Asp|Gly|Ile|His<br>140|Pro|Gly|Ala|Asp|
|Ala<br>145|Glu|Leu|Arg|Pro|Glu<br>150|Leu|Ala|Glu|Phe|Asp<br>155|Leu|Asp|Arg|Leu|Pro<br>160|
|Leu|Pro|Asp|Val|Phe<br>165|Val|Asp|Ile|Cys|Pro<br>170|Pro|Ser|Leu|Arg|Pro<br>175|Ala|
|Gly|Ala|Ala|Pro<br>180|Ala|Gln|Pro|Met|Arg<br>185|Tyr|Val|Pro|Ala|Asn<br>190|Ala|Gln|
|Arg|Arg|Leu<br>195|Glu|Pro|Trp|Met|Tyr<br>200|Arg|Arg|Gly|Glu|Arg<br>205|Arg|Arg|Val|
|Leu<br>210|Val|Thr|Ser|Gly|Ser<br>215|Arg|Val|Ala|Lys|Glu<br>220|Ser|Tyr|Asp|Lys|Asn|
|Phe<br>225|Glu|Phe|Leu|Arg|Gly<br>230|Leu|Ala|Lys|Asp|Val<br>235|Ala|Ala|Trp|Asp|Val<br>240|
|Glu|Leu|Ile|Val|Ala<br>245|Ala|Pro|Glu|Ala|Val<br>250|Ala|Asp|Ala|Leu|His<br>255|Asp|
|Glu|Leu|Pro|Gly<br>260|Ile|Arg|Ala|Gly|Trp<br>265|Ala|Pro|Leu|Asp|Val<br>270|Val|Ala|
|Pro|Thr|Cys<br>275|Asp|Val|Leu|Val|His<br>280|His|Gly|Gly|Gly|Val<br>285|Ser|Thr|Leu|
|Thr|Gly<br>290|Leu|Asn|Ala|Gly|Val<br>295|Pro|Gln|Leu|Leu|Ile<br>300|Pro|Arg|Gly|Ala|
|Val<br>305|Leu|Glu|Lys|Pro|Ala<br>310|Leu|Arg|Val|Ala|Asp<br>315|His|Gly|Ala|Ala|Ile<br>320|
|Thr|Leu|Leu|Pro|Gly<br>325|Glu|Asp|Ala|Ala|Asp<br>330|Ala|Ile|Ala|Asp|Ser<br>335|Cys|
|Gln|Glu|Leu|Leu<br>340|Ser|Lys|Asp|Thr|Tyr<br>345|Gly|Glu|Arg|Ala|Arg<br>350|Glu|Leu|
|Ser|Arg|Glu<br>355|Ile|Ala|Ala|Met|Pro<br>360|Ser|Pro|Ala|Ser|Val<br>365|Val|Asp|Ala|
|Leu|Glu<br>370|Pro|Ala| | | | | | | | | | | | |

( 2 ) INFORMATION FOR SEQ ID NO:34:

( i ) SEQUENCE CHARACTERISTICS:
        ( A ) LENGTH: 355 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

| | | | | | | | | | | | | | | |
|---|---|---|---|---|---|---|---|---|---|---|---|---|---|---|
|Met<br>1|Lys|Ala|Leu|Val<br>5|Leu|Ala|Gly|Gly|Ser<br>10|Gly|Thr|Arg|Leu|Arg<br>15|Pro|
|Phe|Ser|Tyr|Ser<br>20|Met|Pro|Lys|Gln|Leu<br>25|Ile|Pro|Ile|Ala|Asn<br>30|Thr|Pro|
|Val|Leu|Val<br>35|His|Val|Leu|Asn|Ala<br>40|Val|Arg|Glu|Leu|Gly<br>45|Val|Thr|Glu|
|Val|Gly<br>50|Val|Ile|Val|Gly|Asn<br>55|Arg|Gly|Pro|Glu|Ile<br>60|Glu|Ala|Val|Leu|

| | | | | | | | | | | | | | | |
|---|---|---|---|---|---|---|---|---|---|---|---|---|---|---|
| Gly 65 | Asp | Gly | Ala | Arg | Phe 70 | Asp | Val | Arg | Ile 75 | Thr | Tyr | Ile | Pro | Gln Asp 80 |
| Ala | Pro | Arg | Gly | Leu 85 | Ala | His | Thr | Val | Ser 90 | Ile | Ala | Arg | Gly | Phe Leu 95 |
| Gly | Asp | Asp | Asp 100 | Phe | Val | Met | Tyr | Leu 105 | Gly | Asp | Asn | Met | Leu 110 | Pro Asp |
| Gly | Val | Thr 115 | Glu | Ile | Ala | Glu | Glu 120 | Phe | Thr | Arg | Gln | Arg 125 | Pro | Ala Ala |
| Gln | Val 130 | Val | Val | His | Lys | Val 135 | Pro | Asp | Pro | Arg | Ser 140 | Phe | Gly | Val Ala |
| Glu 145 | Leu | Gly | Pro | Asp | Gly 150 | Glu | Val | Leu | Arg | Leu 155 | Val | Glu | Lys | Pro Trp 160 |
| Gln | Pro | Arg | Ser | Asp 165 | Met | Ala | Leu | Ile | Gly 170 | Val | Tyr | Phe | Phe | Thr Ala 175 |
| Ala | Ile | His | Gln 180 | Ala | Val | Ala | Ala | Ile 185 | Ser | Pro | Ser | Ser | Arg 190 | Gly Glu |
| Leu | Glu | Ile 195 | Thr | Asp | Ala | Val | Gln 200 | Trp | Leu | Val | Thr | Ser 205 | Gly | Ala Asp |
| Val | Arg 210 | Ala | Ser | Leu | Tyr | Asp 215 | Gly | Tyr | Trp | Lys | Asp 220 | Thr | Gly | Arg Val |
| Glu 225 | Asp | Val | Leu | Glu | Cys 230 | Asn | Ser | His | Leu | Leu 235 | Asp | Gly | Leu | Thr Pro 240 |
| Arg | Val | Asp | Gly | Gln 245 | Val | Asp | Ala | Asp | Ser 250 | Val | Leu | Val | Gly | Arg Val 255 |
| Val | Ile | Glu | Ala 260 | Gly | Ala | Arg | Ile | Val 265 | Arg | Ser | Arg | Val | Glu 270 | Gly Pro |
| Ala | Ile | Ile 275 | Gly | Ala | Gly | Thr | Val 280 | Leu | Gln | Asp | Ser | Gln 285 | Val | Gly Pro |
| His | Thr 290 | Ser | Ile | Gly | Arg | Asp 295 | Cys | Thr | Val | Thr | Asp 300 | Ser | Arg | Leu Glu |
| Gly 305 | Ser | Ile | Ala | Leu | Asp 310 | Glu | Ala | Ser | Val | Thr 315 | Gly | Val | Arg | Gly Leu 320 |
| Arg | Asn | Ser | Leu | Ile 325 | Gly | Arg | Ala | Ala | Ser 330 | Val | Gly | Thr | Thr | Gly Pro 335 |
| Gly | Thr | Gly | His 340 | His | Cys | Leu | Val | Val 345 | Gly | Asp | His | Thr | Arg 350 | Val Glu |
| Val | Ala | Ala 355 | | | | | | | | | | | | |